US012778530B2

(12) United States Patent
Rooney et al.

(10) Patent No.: US 12,778,530 B2
(45) Date of Patent: Nov. 3, 2026

(54) TOUCH AND MOVE ANATOMY LOCALIZATION

(71) Applicant: Medtronic Navigation, Inc., Louisville, CO (US)

(72) Inventors: Elizabeth Rose Rooney, Waltham, MA (US); Erica C. Freund, Cambridge, MA (US); Xavier Tomas Fernandez, Medford, MA (US); Seunghoon Nam, Bedford, MA (US); Robert Allen Simpson, Shirley, MA (US)

(73) Assignee: Medtronic Navigation, Inc., Louisville, CO (US)

( * ) Notice: Subject to any disclaimer, the term of this patent is extended or adjusted under 35 U.S.C. 154(b) by 143 days.

(21) Appl. No.: 18/656,226

(22) Filed: May 6, 2024

(65) Prior Publication Data

US 2024/0407745 A1 Dec. 12, 2024

Related U.S. Application Data

(60) Provisional application No. 63/472,061, filed on Jun. 9, 2023.

(51) Int. Cl.
*A61B 6/00* (2024.01)
*A61B 6/46* (2024.01)

(52) U.S. Cl.
CPC ............ *A61B 6/488* (2013.01); *A61B 6/4435* (2013.01); *A61B 6/463* (2013.01); *A61B 6/467* (2013.01); *A61B 6/547* (2013.01)

(58) Field of Classification Search
CPC ....... A61B 6/488; A61B 6/4435; A61B 6/465; A61B 6/469; A61B 6/467; A61B 6/545; A61B 6/032; A61B 6/547; A61B 6/463; A61B 6/04; A61B 6/54; A61B 6/461; A61B 6/5211; A61B 6/4464; A61B 34/10; A61B 34/20; A61B 17/8863; A61B 6/505; A61B 6/4441; A61B 6/487; A61B 6/588; A61B 6/589; A61B 6/587; A61B 6/06; A61B 6/102; A61B 6/08; A61B 2090/3966; A61B 2090/3762; A61B 2034/2055; A61B 6/4208; A61B 6/5241; A61B 6/544;

(Continued)

(56) References Cited

U.S. PATENT DOCUMENTS 6,940,941 B2 9/2005 Gregerson et al.
7,001,045 B2 2/2006 Gregerson et al.

(Continued)

OTHER PUBLICATIONS

Newell et al. "An intraoperative fluoroscopic method to accurately measure the post-implantation position of pedicle screws," International Journal of Computer Assisted Radiology and Surgery, Apr. 2018, vol. 13, No. 8, pp. 1257-1267.

(Continued)

*Primary Examiner* — Irakli Kiknadze
(74) *Attorney, Agent, or Firm* — Sheridan Ross PC

(57) ABSTRACT

A system may perform a preview scan process associated with scanning a patient anatomy. Performing the preview scan process may include capturing one or more localization images comprising a portion of the patient anatomy. The system may capture one or more multidimensional images including at least the portion of the patient anatomy based on target coordinates associated with the one or more localization images.

20 Claims, 14 Drawing Sheets

(58) Field of Classification Search

CPC ..... A61B 6/405; A61B 6/4085; A61B 6/4266; A61B 6/5235; A61B 5/0037; A61B 5/055; A61B 6/5247; A61B 6/4447; A61B 6/5264; A61B 6/5294; A61B 6/0407; A61B 8/0841; A61B 6/035; A61B 6/0487; A61B 6/542; A61B 6/0492; A61B 6/037; A61B 34/30; A61B 34/35; A61B 5/1127; A61B 5/742; A61B 90/00; A61B 90/361; A61B 90/37; A61B 90/50; A61B 2034/105; A61B 2034/2048; A61B 2034/2057; A61B 2034/2059; A61B 2034/2065; A61B 2034/2072; A61B 2090/365; A61B 2090/367; A61B 2090/372; A61B 2090/373; A61B 2090/374; A61B 2090/376; A61B 2090/378; A61B 2090/3983; A61B 2560/0223; A61B 2560/0431; A61B 5/0035; A61B 5/7425; G16H 20/40; G16H 50/50; G16H 30/40; G06T 7/33; G06T 7/73; G06T 7/11; G06T 7/0012; G06T 2200/04; G06T 2207/10121; G06T 2207/10081; G06T 2207/30012; G06T 2207/20104; G06T 2207/10116; G06T 2207/10028; G06T 2207/10088; G06T 2207/20221; G06T 7/75; G06T 2207/30008; G06T 2207/20084; G06T 2207/20081; G06T 7/20; G06T 7/70; G06T 7/0014; G06T 2207/10016; G06T 2207/10072; G06T 2207/10132; G06T 2207/10024; G06T 2207/30004; G06T 2207/30196; G06T 2207/10104; G06T 15/08; G06T 15/20; G06T 19/006; G06T 7/248; G06T 7/74; G06N 3/02; H04N 23/60; H04N 23/90; H04N 23/30; H04N 23/698; G06V 10/25; G06V 40/10; G06F 3/04883; G06F 3/1446

USPC ................................................ 378/4, 19, 62

See application file for complete search history.

(56) References Cited

U.S. PATENT DOCUMENTS

| | | | |
|---|---|---|---|
| 7,106,825 B2 | 9/2006 | Gregerson et al. | |
| 7,108,421 B2 | 9/2006 | Gregerson et al. | |
| 7,188,998 B2 | 3/2007 | Gregerson et al. | |
| 2017/0150935 A1 | 6/2017 | Hansis et al. | |
| 2017/0367645 A1 | 12/2017 | Klinder et al. | |
| 2019/0320995 A1 | 10/2019 | Amiri | |
| 2020/0268473 A1* | 8/2020 | Gregerson | A61B 34/20 |
| 2022/0160322 A1 | 5/2022 | Homan et al. | |

OTHER PUBLICATIONS

International Search Report and Written Opinion for International (PCT) Patent Application No. PCT/US2024/032360, dated Sep. 20, 2024 12 pages.

* cited by examiner

TOUCH AND MOVE ANATOMY LOCALIZATION

CROSS REFERENCE TO RELATED APPLICATIONS

This application claims the benefit of U.S. Provisional Application No. 63/472,061, filed on Jun. 9, 2023, and entitled "Touch and Move Anatomy Localization", which application is incorporated herein by reference in its entirety.

FIELD OF INVENTION

The present disclosure is generally directed to imaging, and relates more particularly to surgical imaging.

BACKGROUND

Surgical robots may assist a surgeon or other medical provider in carrying out a surgical procedure, or may complete one or more surgical procedures autonomously. Imaging may be used by a medical provider for diagnostic and/or therapeutic purposes. Patient anatomy can change over time, particularly following placement of a medical implant in the patient anatomy.

BRIEF SUMMARY

Example aspects of the present disclosure include:

An imaging system including: a processor coupled with the imaging system; and a memory storing instructions thereon that, when executed by the processor, cause the processor to: perform a preview scan process associated with scanning a patient anatomy, wherein performing the preview scan process includes capturing one or more localization images including a portion of the patient anatomy; and capture one or more multidimensional images including at least the portion of the patient anatomy based on target coordinates associated with the one or more localization images.

Any of the aspects herein, wherein the instructions are further executable by the processor to: based on the target coordinates, generate movement data associated with positioning or orienting at least one of a radiation source, a detector, a rotor, and a gantry of the imaging system in association with capturing the one or more multidimensional images.

Any of the aspects herein, wherein the instructions are further executable by the processor to: control the positioning or orienting of at least one of the radiation source, the detector, the rotor, and the gantry based on the movement data.

Any of the aspects herein, wherein the instructions are further executable by the processor to: display guidance information associated with the positioning or orienting of at least one of the radiation source, the detector, the rotor, and the gantry based on the movement data.

Any of the aspects herein, wherein generating the movement data is based on: a pixel size associated with the one or more localization images; and a focal plane associated with the preview scan process.

Any of the aspects herein, wherein the one or more localization images include: a first localization image of a first image type including the portion of the patient anatomy; and a second localization image of a second image type including the portion of the patient anatomy, wherein capturing the one or more multidimensional images is based on at least one of the first localization image and the second localization image.

Any of the aspects herein, wherein the instructions are further executable by the processor to: set the target coordinates in response to a user input associated with the imaging system.

Any of the aspects herein, wherein the user input includes an input via at least one of: a display; a controller device; and an audio input device.

Any of the aspects herein, wherein the instructions are further executable by the processor to: generate a field of view representation of the patient anatomy including the one or more localization images; and update the field of view representation based on the target coordinates.

Any of the aspects herein, wherein the instructions are further executable by the processor to: capture one or more second localization images including the portion of the patient anatomy based on the target coordinates, wherein capturing the one or more multidimensional images is based on: the one or more second localization images; one or more second target coordinates associated with the one or more second localization images; or both.

Any of the aspects herein, wherein the instructions executable to capture the one or more multidimensional images are further executable by the processor to capture an image volume including at least the portion of the patient anatomy based on image data of the one or more multidimensional images.

Any of the aspects herein, wherein the instructions are further executable by the processor to generate a long scan image including at least the portion of the patient anatomy based on image data of the one or more multidimensional images.

Any of the aspects herein, wherein each of the one or more localization images is: an anterior-posterior image, a posterior-anterior image, a lateral image, an oblique image, an axial image, a coronal image, or a sagittal image.

Any of the aspects herein, wherein capturing the one or more localization images is based on: one or more positions of a radiation source of the imaging system; and pose information of a subject with respect to the imaging system.

Any of the aspects herein, wherein the instructions are further executable by the processor to: display orientation information associated with the patient anatomy and the one or more localization images.

Any of the aspects herein, wherein: the one or more localization images include a first localization image and a second localization image; and the instructions are further executable by the processor to: pause setting of second target coordinates in association with the second localization image in response to detecting an active user input of setting first target coordinates in association with the first localization image; and enable the setting of the second target coordinates in response to detecting completion of the active user input.

A system including: a processor; and a memory storing instructions thereon that, when executed by the processor, cause the processor to: perform a preview scan process associated with scanning a patient anatomy, wherein performing the preview scan process includes capturing one or more localization images including a portion of the patient anatomy; and capture one or more multidimensional images including at least the portion of the patient anatomy based on target coordinates associated with the one or more localization images.

Any of the aspects herein, wherein the instructions are further executable by the processor to: based on the target coordinates, generate movement data associated with positioning or orienting at least one of a radiation source, a detector, a rotor, and a gantry of the system in association with capturing the one or more multidimensional images.

Any of the aspects herein, wherein the instructions are further executable by the processor to: control the positioning or orienting of at least one of the radiation source, the detector, the rotor, and the gantry based on the movement data; display guidance information associated with the positioning or orienting of at least one of the radiation source, the detector, the rotor, and the gantry based on the movement data; or a combination thereof.

In some aspects, the techniques described herein relate to a method including: performing, by an imaging system, a preview scan process associated with scanning a patient anatomy, wherein performing the preview scan process includes capturing one or more localization images including a portion of the patient anatomy; and capturing one or more multidimensional images including at least the portion of the patient anatomy based on target coordinates associated with the one or more localization images.

In some aspects, the techniques described herein relate to an imaging system including: a processor coupled with the imaging system; and a memory storing instructions thereon that, when executed by the processor, cause the processor to: generate an image including a patient anatomy and one or more implanted medical devices based on performing a long scan process associated with scanning the patient anatomy, wherein generating the image includes sizing a first representation of the patient anatomy and a second representation of the one or more implanted medical devices in the image based on: a pixel size associated with the image; and a focal plane associated with the long scan process; and display the image and a surgical plan associated with the patient anatomy at a user interface of the imaging system, wherein displaying the image and the surgical plan includes at least partially overlaying the surgical plan over the image.

Any of the aspects herein, wherein: the surgical plan includes a graphical model of the one or more implanted medical devices; and displaying the image and the surgical plan includes displaying the graphical model in combination with at least one of: the first representation of the patient anatomy; and the second representation of the one or more implanted medical devices.

Any of the aspects herein, wherein the instructions are further executable by the processor to: scale a size of the graphical model based on the pixel size associated with the image.

Any of the aspects herein, wherein: the surgical plan includes labeling information associated with the patient anatomy; and the instructions are further executable by the processor to position the graphical model with respect to the first representation of the patient anatomy based on: the labeling information; and pixels corresponding to the patient anatomy from among a plurality of pixels associated with the image.

Any of the aspects herein, wherein the instructions are further executable by the processor to adjust, based on one or more scaling factors, at least one of: a first size of the first representation of the patient anatomy; a second size of the second representation of the one or more implanted medical devices; and a third size of the graphical model of the one or more implanted medical devices.

Any of the aspects herein, wherein the image includes a long scan image.

Any of the aspects herein, wherein the instructions are further executable by the processor to: scale a size of the first representation of the patient anatomy with reference to a physical size of the patient anatomy in one or more dimensions.

Any of the aspects herein, wherein the instructions are further executable by the processor to: scale a size of the second representation of the one or more implanted medical devices with reference to a physical size of the one or more implanted medical devices in one or more dimensions.

Any of the aspects herein, wherein the instructions are further executable by the processor to: update a pixel size associated with the image based on a change in focus level associated with generating the image, wherein displaying the image is based on the updated pixel size.

Any of the aspects herein, wherein: the surgical plan includes one or more preoperative images, one or more reference intraoperative images, or both; and the image includes one or more second intraoperative images, one or more postoperative images, or both.

Any of the aspects herein, wherein the image includes an X-ray image, a computed tomography (CT) image, or a magnetic resonance imaging (MRI) image.

A system including: a processor; and a memory storing instructions thereon that, when executed by the processor, cause the processor to: generate an image including a patient anatomy and one or more implanted medical devices based on performing a long scan process associated with scanning the patient anatomy, wherein generating the image includes sizing a first representation of the patient anatomy and a second representation of the one or more implanted medical devices in the image based on: a pixel size associated with the image; and a focal plane associated with the long scan process; and display the image and a surgical plan associated with the patient anatomy at a user interface of the system, wherein displaying the image and the surgical plan includes at least partially overlaying the surgical plan over the image.

Any of the aspects herein, wherein: the surgical plan includes a graphical model of the one or more implanted medical devices; and displaying the image and the surgical plan includes displaying the graphical model in combination with at least one of: the first representation of the patient anatomy; and the second representation of the one or more implanted medical devices.

Any of the aspects herein, wherein the instructions are further executable by the processor to: scale a size of the graphical model based on the pixel size associated with the image.

Any of the aspects herein, wherein: the surgical plan includes labeling information associated with the patient anatomy; and the instructions are further executable by the processor to position the graphical model with respect to the first representation of the patient anatomy based on: the labeling information; and pixels corresponding to the patient anatomy from among a plurality of pixels associated with the image.

Any of the aspects herein, wherein the instructions are further executable by the processor to adjust, based on one or more scaling factors, at least one of: a first size of the first representation of the patient anatomy; a second size of the second representation of the one or more implanted medical devices; and a third size of the graphical model of the one or more implanted medical devices.

Any of the aspects herein, wherein the instructions are further executable by the processor to: scale a size of the first representation of the patient anatomy with reference to a physical size of the patient anatomy in one or more dimensions.

Any of the aspects herein, wherein the instructions are further executable by the processor to: scale a size of the second representation of the one or more implanted medical devices with reference to a physical size of the one or more implanted medical devices in one or more dimensions.

Any of the aspects herein, wherein the instructions are further executable by the processor to: update a pixel size associated with the image based on a change in focus level associated with generating the image, wherein displaying the image is based on the updated pixel size.

In some aspects, the techniques described herein relate to a method including: generating an image including a patient anatomy and one or more implanted medical devices based on performing a long scan process associated with scanning the patient anatomy, wherein generating the image includes sizing a first representation of the patient anatomy and a second representation of the one or more implanted medical devices in the image based on: a pixel size associated with the image; and a focal plane associated with the long scan process; and displaying the image and a surgical plan associated with the patient anatomy at a user interface, wherein displaying the image and the surgical plan includes at least partially overlaying the surgical plan over the image.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/implementations in combination with any one or more other aspects/features/implementations.

Use of any one or more of the aspects or features as disclosed herein.

It is to be appreciated that any feature described herein can be claimed in combination with any other feature(s) as described herein, regardless of whether the features come from the same described implementation.

The details of one or more aspects of the disclosure are set forth in the accompanying drawings and the description below. Other features, objects, and advantages of the techniques described in this disclosure will be apparent from the description and drawings, and from the claims.

The preceding is a simplified summary of the disclosure to provide an understanding of some aspects of the disclosure. This summary is neither an extensive nor exhaustive overview of the disclosure and its various aspects, implementations, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, implementations, and configurations of the disclosure are possible utilizing, alone or in combination, one or more of the features set forth above or described in detail below.

Numerous additional features and advantages of the present disclosure will become apparent to those skilled in the art upon consideration of the implementation descriptions provided hereinbelow.

BRIEF DESCRIPTION OF THE SEVERAL VIEWS OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, implementations, and configurations of the disclosure, as illustrated by the drawings referenced below.

DETAILED DESCRIPTION

Figure 1A:
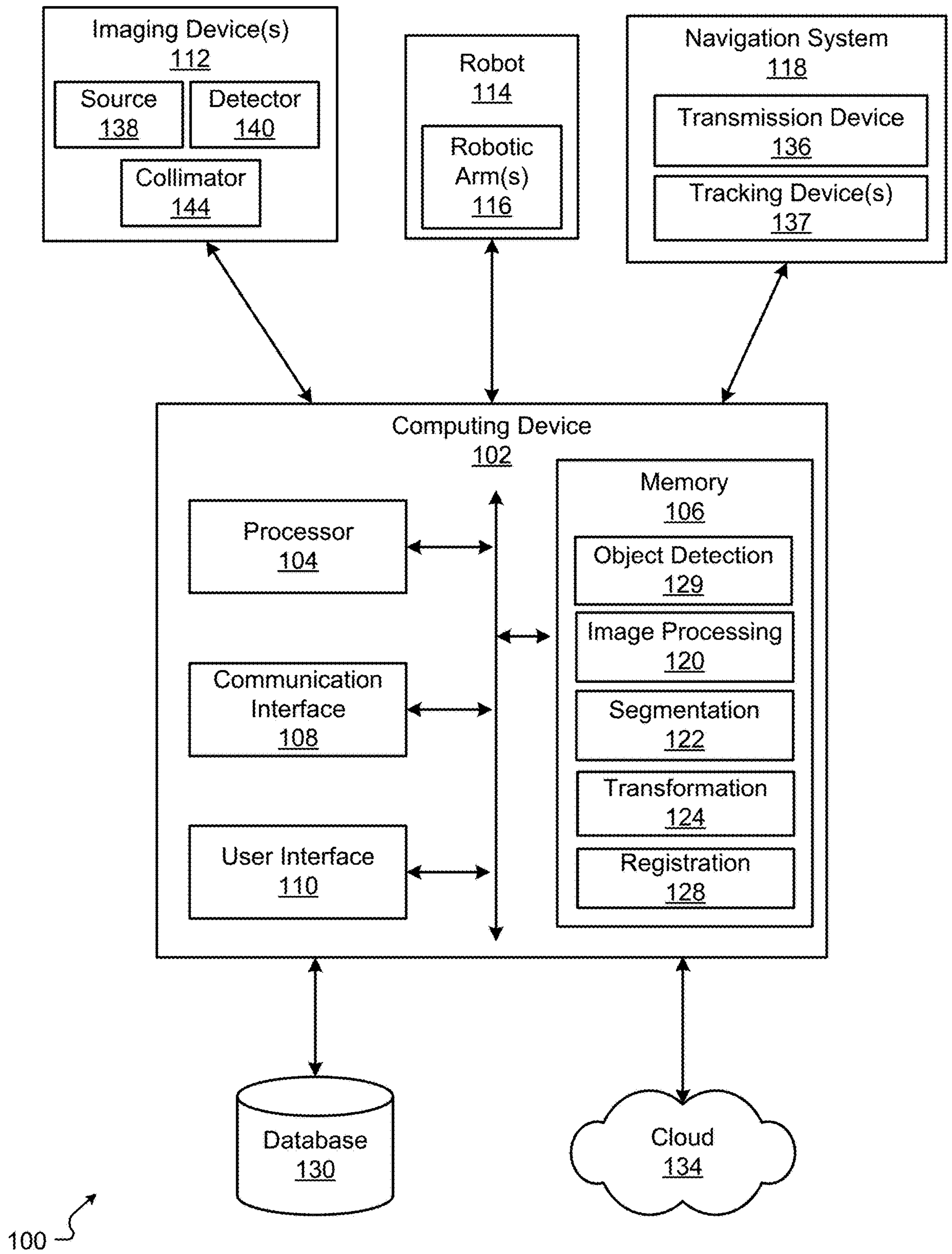
FIGS. 1A through ID illustrate examples of a system in accordance with aspects of the present disclosure.

It should be understood that various aspects disclosed herein may be combined in different combinations than the combinations specifically presented in the description and accompanying drawings. It should also be understood that, depending on the example or implementation, certain acts or events of any of the processes or methods described herein may be performed in a different sequence, and/or may be added, merged, or left out altogether (e.g., all described acts or events may not be necessary to carry out the disclosed techniques according to different implementations of the present disclosure). In addition, while certain aspects of this disclosure are described as being performed by a single module or unit for purposes of clarity, it should be understood that the techniques of this disclosure may be performed by a combination of units or modules associated with, for example, a computing device and/or a medical device.

In one or more examples, the described methods, processes, and techniques may be implemented in hardware, software, firmware, or any combination thereof. If implemented in software, the functions may be stored as one or more instructions or code on a computer-readable medium and executed by a hardware-based processing unit. Alternatively or additionally, functions may be implemented using machine learning models, neural networks, artificial neural networks, or combinations thereof (alone or in combination with instructions). Alternatively or additionally, functions may be implemented using machine learning models, neural networks, artificial neural networks, or combinations thereof (alone or in combination with instructions). Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors (e.g., Intel Core i3, i5, i7, or i9 processors; Intel Celeron processors; Intel Xeon processors; Intel Pentium processors; AMD Ryzen processors; AMD Athlon processors; AMD Phenom processors; Apple A10 or 10X Fusion processors; Apple A11, A12, A12X, A12Z, or A13 Bionic processors; or any other general purpose microprocessors), graphics processing units (e.g., Nvidia Geforce RTX 2000-series processors, Nvidia Geforce RTX 3000-series processors, AMD Radeon RX 5000-series processors, AMD Radeon RX 6000-series processors, or any other graphics processing units), application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

Before any implementations of the disclosure are explained in detail, it is to be understood that the disclosure is not limited in its application to the details of construction and the arrangement of components set forth in the following description or illustrated in the drawings. The disclosure is capable of other implementations and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Further, the present disclosure may use examples to illustrate one or more aspects thereof. Unless explicitly stated otherwise, the use or listing of one or more examples (which may be denoted by "for example," "by way of example," "e.g.," "such as," or similar language) is not intended to and does not limit the scope of the present disclosure.

The terms proximal and distal are used in this disclosure with their conventional medical meanings, proximal being closer to the operator or user of the system, and further from the region of surgical interest in or on the patient, and distal being closer to the region of surgical interest in or on the patient, and further from the operator or user of the system.

Some imaging systems may support capturing "scout images" (also referred to herein as "localization images") prior to a subsequent scan. For example, scout images may provide a user with a survey of a region of interest. The scout images may provide anatomical information based on which the system or a user may localize a target patient anatomy.

Some imaging systems may support a long scan process capable of generating a multidimensional "long scan" (also referred to herein as a "long film," "long film image," or "pseudo-panoramic image") of a patient anatomy using an imaging device. For example, performing a long scan may produce a long film based on multiple images captured by an imaging device, which may provide a relatively longer or wider image compared to an individual image captured by the imaging device.

Some imaging systems may support capturing an image volume of a patient anatomy using an imaging device. In some radiological imaging workflows associated with taking a 3D image volume of a patient anatomy, the workflow may include acquiring capturing 2D "scout images" (also referred to herein as "localization images") prior to a subsequent scan for capturing the 3D image volume. For example, based on the 2D scout images, a user (e.g., radiology technician) may confirm that the anatomy has been captured for a surgical procedure.

The O-Arm® imaging system provided by Medtronic Navigation, Inc. supports providing a field of view (FOV) preview feature (also referred to herein as a FOV preview representation and a multiple FOV representation). Via the FOV preview representation, a user may view an acquired 2D scout image, to determine whether a patient is centered for a subsequent scanning procedure (e.g., long scan process, volume scan, etc.). In some cases, a user may become quickly disoriented in understanding how to position or move the imaging system in order to center the imaging system on a target patient anatomy.

Accordingly, for example, in some cases, the imaging system may be unsuccessful at capturing the target patient anatomy in the subsequent scanning procedure, which may result in additional attempts of performing the scanning procedure to capture the target patient anatomy. The additional attempts may result in increased radiation dose to the patient and increased time associated with the surgical workflow.

Aspects of the present disclosure support enhancements to the FOV preview feature. The systems and techniques described herein support features to increase usability and simplify an imaging workflow through an interface supportive of patient orientation inputs. In some aspects, the interface and patient orientation input support may provide users the ability to view a 2D scout image and select, on the 2D scout image, target coordinates to which the user wishes an imaging system to move. The system may support user input of the target coordinates via a touchscreen monitor displaying the 2D scout image, a controller device, an audio input device, and the like.

In an example, based on a user selection of target coordinates (e.g., via a touch input at the touchscreen monitor, via a user input at the controller device, etc.), the system may calculate movement data associated with moving and/or positioning components (e.g., an imaging device, a table supporting a patient, etc.) of an imaging system with respect to the target coordinates. For example, the system may calculate movement data associated with positioning the components to reach the location corresponding to the target coordinates. In some aspects, the system may move the one or more components according to the movement data in response to a further user input (e.g., a user input of pressing a holding a button of a controller device, a user input of touching and holding a virtual button on the touchscreen monitor, etc.).

The system may calculate one or more axes of motion (e.g., with respect to an X-axis, a Y-axis, or Z-axis of a coordinate system) for positioning the components based on 2D scout images captured by the system. In an example, the system may calculate movement data with respect to 2 axes of motion from a single 2D scout image. In another example, the system may calculate movement data with respect to 3 axes of motion from two 2D scout images (e.g., an anterior-posterior (AP) image and a lateral image).

Accordingly, for example, the systems and techniques described herein provide features which may reduce or remove the cognitive load from a user with respect to positioning components of an imaging system to reach a target anatomy location, as the systems and techniques include automatically calculating movement data for positioning the components based on target coordinates set by the user. Aspects of the present disclosure support a system which may position or move components of the imaging system to reach different anatomy locations, even for cases in which a user understanding of how to position or move the components is relatively low. In an example, the system may lessen the cognitive load on the user with respect to understanding the orientation of a 2D scout image and how the orientation relates to system motion.

In some examples, reducing the cognitive load for a user may be beneficial in use cases (e.g., cranial use cases, etc.) in which a patient is positioned at an angle with respect to an imaging system and multiple axes of motion are involved for moving components of the imaging system along the patient axis. The touch and move capabilities supported by aspects of the present disclosure may streamline the anatomy localization step in a user workflow (e.g., through increased speed and efficiency) and reduce patient dose, for example, by reducing the number of 2D scout images captured in association with positioning the patient anatomy for a subsequent scanning process (e.g., 3D image acquisition, long scan image acquisition, etc.).

In some example aspects, in response to a user input indicating a target (e.g., a target anatomy of a patient, target coordinates, target boundaries, etc.) on a localization image, the system may position components (e.g., source, detector, gantry, etc.) of an imaging system and/or position a patient such that the imaging system may capture one or more multidimensional images including the target. In some aspects, the multidimensional images may be long scan images captured using a long scan process. In some other aspects, the multidimensional images may be 3D images captured in association with capturing an image volume.

The systems and techniques described herein may support manual system motion, which may include generating and providing guidance information (e.g., movement data, spatial coordinates, etc.) for positioning the imaging system and/or the patient in association with capturing multidimensional images with respect to a subsequent scan (e.g., a long scan image, a 3D image volume, etc.) and/or capturing additional localization images. Additionally, or alternatively, the systems and techniques described herein may support automatic movement of the imaging system as described herein. For example, the systems and techniques may include translating a user input (e.g., a target object, target coordinates, target boundaries, etc.) into system positioning commands and source-detector acquisition motion.

According to example aspects of the present disclosure, the combination of the FOV preview capability, localization images, and automatic calculation of movement data based on user inputs (e.g., touch and go features) may assist a user in association with localizing target anatomical structures with minimal radiation dose. Accordingly, for example, the techniques described herein may minimize patient and operator risk and increase safety associated with the use of an imaging system, while improving user confidence that patient anatomy for a surgical procedure will be captured in a subsequent scan (e.g., a long scan image, a 3D image volume, etc.). In some examples, the systems and techniques described herein support FOV preview capability, localization images, and automatic calculation of movement data as described herein in conjunction with multiple imaging types (e.g., X-ray imaging, computed tomography (CT) imaging, magnetic resonance imaging (MRI), ultrasound imaging, optical imaging, light detection and ranging (LiDAR) imaging, camera images from an O-arm, preoperative images, intraoperative images, etc.).

Examples of localization images described herein include an X-ray image, a CT image, an MRI image, an optical image, and a LiDAR image, but are not limited thereto. Examples of multidimensional images captured based on the localization images as described herein include an X-ray image, a CT image, and an MRI image, but are not limited thereto.

According to example aspects of the present disclosure, the systems and techniques described herein provide features which support increased speed and efficiency associated with 2D image anatomy localization. The features described herein may support increased success associated with moving or positioning components of an imaging system in association with focusing an imaging system on a target anatomy of interest.

Implementations of the present disclosure provide technical solutions to one or more of the problems of radiation exposure to operators, surgeons, and patients. X-ray exposure can be quantified by dose, or the amount of energy deposited by radiation in tissue. Ionizing radiation can cause debilitating medical conditions. The techniques described herein of combining the FOV preview capability and system-based calculation of movement data (also referred to herein as system motion calculations) for an imaging system may reduce the risk of inadvertently capturing a multidimensional image (e.g., long scan image, image volume, etc.) which fails to capture an entire anatomy of interest. Accordingly, for example, the systems and techniques may reduce additional radiation exposure associated with capturing additional 2D scout images for localizing the patient anatomy and recapturing the multidimensional image. The techniques described herein may allow operators of an imaging system (e.g., an O-arm system) to complete operations of a radiological imaging workflow with increased efficiency and speed.

Other aspects of the present disclosure support to-scale representation of patient anatomy relative to implanted medical devices. The systems and techniques described herein support to-scale representation using known pixel size of 2D radiographic image (e.g., a long scan image described herein). The systems and techniques described herein include features which may provide technical solutions to one or more of the problems associated with radiography-assisted surgical intervention.

Radiography-assisted surgical intervention is used across medical disciplines. Radiography-assisted surgical intervention provides visualization of internal structures including patient anatomy, surgical instruments, and implanted medical devices. Radiography is used in planning, intervention, and confirmation/reconciliation phases of surgical procedures. For example, spine deformity may be corrected with surgical intervention in which screws and rods are implanted into the bony vertebrae of the spine for support and to create more stable alignment. The spine surgeon can use imaging to plan, perform, and reconcile the hardware placement to ensure the best outcome for the patient.

Distortion or misrepresentation of the size or placement of implanted hardware in a radiographic image may have severe consequences for a patient. Radiographic tools are desired that improve workflow, reduce surgical time, and increase confidence in surgical execution and thereby reduce costs and liability of a provider (e.g., healthcare provider, insurance provider, etc.) and/or hospital/healthcare network.

The systems and techniques described herein support to-scale representation using known pixel size of 2D radiographic image (e.g., a 2D x-ray image) and/or a 3D image to represent the pose of implanted medical devices relative to (e.g., at scale) the patient anatomy for intraoperative planning and/or confirmation. For example, the systems and techniques support representation of the to-scale pose of implanted medical devices relative to actual size of the patient anatomy.

An example workflow supported by aspects of the present disclosure is described herein. The workflow may include creating a surgical plan and choosing implantable device(s) and performing a surgical procedure. The workflow may include acquiring and reconstructing 2D radiographic images with known pixel size and focal plane intraoperatively to visualize patient anatomy, surgical instruments, and/or implanted medical device(s). The workflow may include displaying a to-scale 2D image of internal structures on a digital display. In some aspects, the workflow may include overlaying a preoperative plan (also referred to herein as a preoperative surgical plan) on an interoperative image to assess degree of completion of a surgical plan.

In some aspects, the preoperative plan may include 2D image data and/or 3D image data. For example, the preoperative plan may include one or more 2D preoperative images and/or one or more 3D preoperative images. In some example aspects, the preoperative plan may include metadata associated with a preoperative image(s) included in the preoperative plan. In an example, for a preoperative image(s) (e.g., a 2D image, a 3D image), the metadata may include coordinates of annotations included in the preoperative image(s).

The systems and techniques may support manual or software-based merger of the interoperative image with the preoperative plan. The workflow may include performing one or more additional surgical corrections to meet alignment goals associated with the preoperative plan. Aspects of the present disclosure include marking the workflow as complete based on completion of the alignment goals.

The systems and techniques may support image scaling and object scaling. In an example, the systems and techniques described herein may support scaling the anatomy captured in a 2D image to actual size of the anatomy, using the pixel size of the 2D image. In some other examples, the systems and techniques described herein may support scaling a graphical model of an implanted medical device overlaid on a 2D image, using the pixel size of the 2D image. Accordingly, for example, the systems and techniques may support scaling the graphical model of the implanted medical device with respect to anatomy included in the 2D image.

The systems and techniques may support anatomical detection and labeling. For example, the systems and techniques described herein may support automatically posing a graphical model of an implanted medical device on a 2D image, using pre-existing anatomical detection/labeling of anatomy included in the 2D image.

Aspects of the present disclosure support manual and/or automatic implementations of any of the techniques described herein. In an example implementation, the systems and techniques described herein may support manual focusing with respect to a 2D image to readjust the pixel size of the 2D image (e.g., if the overlay between a preoperative plan and an interoperative image mismatches). In another example implementation, the systems and techniques described herein may support automatic refocusing with respect to a 2D image to readjust the pixel size of the 2D image (e.g., based on a threshold overlay value between the preoperative plan and the interoperative image), mismatches). In some other aspects, the systems and techniques may support manual and/or automatic scaling (e.g., of the patient anatomy in a 2D image, of a graphical model of an implanted medical device, etc.) to adjust the size of the overlay or the size of the 2D image.

Implementations of the present disclosure provide technical solutions to one or more of the problems associated with visualization of anatomical structures. The techniques described herein provide intraoperative 2D x-ray image acquisition strategies and to-scale representation that may support reduced time, increased patient safety, and improved workflow and visualization of target structures (e.g., anatomical elements, implanted medical devices, etc.).

FIGS. 1A through 1D illustrate examples of a system 100 that support aspects of the present disclosure.

Referring to FIG. 1A, the system 100 includes a computing device 102, one or more imaging devices 112, a robot 114, a navigation system 118, a database 130, and/or a cloud network 134 (or other network). Systems according to other implementations of the present disclosure may include more or fewer components than the system 100. For example, the system 100 may omit and/or include additional instances of one or more components of the computing device 102, the imaging device(s) 112, the robot 114, navigation system 118, the database 130, and/or the cloud network 134. In an example, the system 100 may omit any instance of the computing device 102, the imaging device(s) 112, the robot 114, navigation system 118, the database 130, and/or the cloud network 134. The system 100 may support the implementation of one or more other aspects of one or more of the methods disclosed herein.

The computing device 102 includes a processor 104, a memory 106, a communication interface 108, and a user interface 110. Computing devices according to other implementations of the present disclosure may include more or fewer components than the computing device 102. The computing device 102 may be, for example, a control device including electronic circuitry associated with controlling any of the imaging device 112, the robot 114, and the navigation system 118.

The processor 104 of the computing device 102 may be any processor described herein or any similar processor. The processor 104 may be configured to execute instructions stored in the memory 106, which instructions may cause the processor 104 to carry out one or more computing steps utilizing or based on data received from the imaging devices 112, the robot 114, the navigation system 118, the database 130, and/or the cloud network 134.

The memory 106 may be or include RAM, DRAM, SDRAM, other solid-state memory, any memory described herein, or any other tangible, non-transitory memory for storing computer-readable data and/or instructions. The memory 106 may store information or data associated with completing, for example, any step of the process flows 300 and 400 described herein, or of any other methods. The memory 106 may store, for example, instructions and/or machine learning models that support one or more functions of the imaging devices 112, the robot 114, and the navigation system 118. For instance, the memory 106 may store content (e.g., instructions and/or machine learning models) that, when executed by the processor 104, enable image processing 120, segmentation 122, transformation 124, registration 128, and/or object detection 129. Such content, if provided as in instruction, may, in some implementations, be organized into one or more applications, modules, packages, layers, or engines.

Alternatively or additionally, the memory 106 may store other types of content or data (e.g., machine learning models, artificial neural networks, deep neural networks, etc.) that can be processed by the processor 104 to carry out the various method and features described herein. Thus, although various contents of memory 106 may be described as instructions, it should be appreciated that functionality described herein can be achieved through use of instructions, algorithms, and/or machine learning models. The data, algorithms, and/or instructions may cause the processor 104 to manipulate data stored in the memory 106 and/or received from or via the imaging devices 112, the robot 114, the navigation system 118, the database 130, and/or the cloud network 134.

The computing device 102 may also include a communication interface 108. The communication interface 108 may be used for receiving data or other information from an external source (e.g., the imaging devices 112, the robot 114, the navigation system 118, the database 130, the cloud network 134, and/or any other system or component separate from the system 100), and/or for transmitting instructions, data (e.g., image data, etc.), or other information to an external system or device (e.g., another computing device 102, the imaging devices 112, the robot 114, the navigation system 118, the database 130, the cloud network 134, and/or any other system or component not part of the system 100). The communication interface 108 may include one or more wired interfaces (e.g., a USB port, an Ethernet port, a Firewire port) and/or one or more wireless transceivers or interfaces (configured, for example, to transmit and/or receive information via one or more wireless communication protocols such as 802.11a/b/g/n, Bluetooth, NFC, ZigBee, and so forth). In some implementations, the communication interface 108 may support communication between the device 102 and one or more other processors 104 or computing devices 102, whether to reduce the time needed to accomplish a computing-intensive task or for any other reason.

The computing device 102 may also include one or more user interfaces 110. The user interface 110 may be or include a keyboard, mouse, trackball, monitor, television, screen, touchscreen, and/or any other device for receiving information from a user and/or for providing information to a user. The user interface 110 may be used, for example, to receive a user selection or other user input regarding any step of any method described herein. Notwithstanding the foregoing, any required input for any step of any method described herein may be generated automatically by the system 100 (e.g., by the processor 104 or another component of the system 100) or received by the system 100 from a source external to the system 100. In some implementations, the user interface 110 may support user modification (e.g., by a surgeon, medical personnel, a patient, etc.) of instructions to be executed by the processor 104 according to one or more implementations of the present disclosure, and/or to user modification or adjustment of a setting of other information displayed on the user interface 110 or corresponding thereto.

In some implementations, the computing device 102 may utilize a user interface 110 that is housed separately from one or more remaining components of the computing device 102. In some implementations, the user interface 110 may be located proximate one or more other components of the computing device 102, while in other implementations, the user interface 110 may be located remotely from one or more other components of the computer device 102.

The imaging device 112 may be operable to image anatomical feature(s) (e.g., a bone, veins, tissue, etc.) and/or other aspects of patient anatomy to yield image data (e.g., image data depicting or corresponding to a bone, veins, tissue, etc.). "Image data" as used herein refers to the data generated or captured by an imaging device 112, including in a machine-readable form, a graphical/visual form, and in any other form. In various examples, the image data may include data corresponding to an anatomical feature of a patient, or to a portion thereof. The image data may be or include a preoperative image, an intraoperative image, a postoperative image, or an image taken independently of any surgical procedure. In some implementations, a first imaging device 112 may be used to obtain first image data (e.g., a first image) at a first time, and a second imaging device 112 may be used to obtain second image data (e.g., a second image) at a second time after the first time. The imaging device 112 may be capable of taking a 2D image or a 3D image to yield the image data. The imaging device 112 may be or include, for example, an ultrasound scanner (which may include, for example, a physically separate transducer and receiver, or a single ultrasound transceiver), an O-arm, a C-arm, a G-arm, or any other device utilizing X-ray-based imaging (e.g., a fluoroscope, a CT scanner, or other X-ray machine), a magnetic resonance imaging (MRI) scanner, an optical coherence tomography (OCT) scanner, an endoscope, a microscope, an optical camera, a thermographic camera (e.g., an infrared camera), a radar system (which may include, for example, a transmitter, a receiver, a processor, and one or more antennae), or any other imaging device 112 suitable for obtaining images of an anatomical feature of a patient 148. The imaging device 112 may be contained entirely within a single housing, or may include a transmitter/emitter and a receiver/detector that are in separate housings or are otherwise physically separated.

In some implementations, the imaging device 112 may include more than one imaging device 112. For example, a first imaging device may provide first image data and/or a first image, and a second imaging device may provide second image data and/or a second image. In still other implementations, the same imaging device may be used to provide both the first image data and the second image data, and/or any other image data described herein. The imaging device 112 may be operable to generate a stream of image data. For example, the imaging device 112 may be configured to operate with an open shutter, or with a shutter that continuously alternates between open and shut so as to capture successive images. For purposes of the present disclosure, unless specified otherwise, image data may be considered to be continuous and/or provided as an image data stream if the image data represents two or more frames per second.

The imaging device 112 may include a source 138, a detector 140, and a collimator 144, example aspects of which are later described with reference to FIGS. 1B, 1C, and 1D.

The robot 114 may be any surgical robot or surgical robotic system. The robot 114 may be or include, for example, the Mazor X™ Stealth Edition robotic guidance system. The robot 114 may be configured to position the imaging device 112 at one or more precise position(s) and orientation(s), and/or to return the imaging device 112 to the same position(s) and orientation(s) at a later point in time. The robot 114 may additionally or alternatively be configured to manipulate a surgical tool (whether based on guidance from the navigation system 118 or not) to accomplish or to assist with a surgical task. In some implementations, the robot 114 may be configured to hold and/or manipulate an anatomical element during or in connection with a surgical procedure. The robot 114 may include one or more robotic arms 116. In some implementations, the robotic arm 116 may include a first robotic arm and a second robotic arm, though the robot 114 may include more than two robotic arms. In some implementations, one or more of the robotic arms 116 may be used to hold and/or maneuver the imaging device 112. In implementations where the imaging device 112 includes two or more physically separate components (e.g., a transmitter and receiver), one robotic arm 116 may hold one such component, and another robotic arm 116 may hold another such component. Each robotic arm 116 may be positionable independently of the other robotic arm. The robotic arms 116 may be controlled in a single, shared coordinate space, or in separate coordinate spaces.

The robot 114, together with the robotic arm 116, may have, for example, one, two, three, four, five, six, seven, or more degrees of freedom. Further, the robotic arm 116 may be positioned or positionable in any pose, plane, and/or focal point. The pose includes a position and an orientation. As a result, an imaging device 112, surgical tool, or other object held by the robot 114 (or, more specifically, by the robotic arm 116) may be precisely positionable in one or more needed and specific positions and orientations.

The robotic arm(s) 116 may include one or more sensors that enable the processor 104 (or a processor of the robot 114) to determine a precise pose in space of the robotic arm (as well as any object or element held by or secured to the robotic arm).

In some implementations, reference markers (e.g., navigation markers) may be placed on the robot 114 (including, e.g., on the robotic arm 116), the imaging device 112, or any other object in the surgical space. The reference markers may be tracked by the navigation system 118, and the results of the tracking may be used by the robot 114 and/or by an operator of the system 100 or any component thereof. In some implementations, the navigation system 118 can be used to track other components of the system (e.g., imaging device 112) and the system can operate without the use of the robot 114 (e.g., with the surgeon manually manipulating the imaging device 112 and/or one or more surgical tools, based on information and/or instructions generated by the navigation system 118, for example).

The navigation system 118 may provide navigation for a surgeon and/or a surgical robot during an operation. The navigation system 118 may be any now-known or future-developed navigation system, including, for example, the Medtronic StealthStation™ S8 surgical navigation system or any successor thereof. The navigation system 118 may include one or more cameras or other sensor(s) for tracking one or more reference markers, navigated trackers, or other objects within the operating room or other room in which some or all of the system 100 is located. The one or more cameras may be optical cameras, infrared cameras, or other cameras. In some implementations, the navigation system 118 may include one or more electromagnetic sensors.

In some aspects, the navigation system 118 may include one or more of an optical tracking system, an acoustic tracking system, an electromagnetic tracking system, a radar tracking system, an inertial measurement unit (IMU) based tracking system, and a computer vision based tracking system. The navigation system 118 may include a corresponding transmission device 136 capable of transmitting signals associated with the tracking type. In some aspects, the navigation system 118 may be capable of computer vision based tracking of objects present in images captured by the imaging device(s) 112.

The navigation system 118 may include tracking devices 137. The tracking devices 137 may include or be provided as sensors (also referred to herein as tracking sensors). The system 100 may support the delivery of tracking information associated with the tracking devices 137 to the navigation system 118. The tracking information may include, for example, data associated with signals (e.g., magnetic fields, radar signals, audio signals, etc.) emitted by a transmission device 136 and sensed by the tracking devices 137.

The tracking devices 137 may communicate sensor information to the navigation system 118 for determining a position of the tracked portions relative to each other and/or for localizing an object (e.g., an instrument, an anatomical element, etc.) relative to an image. The navigation system 118 and/or transmission device 136 may include a controller that supports operating and powering the generation of signals to be emitted by the transmission device 136.

In various implementations, the navigation system 118 may be used to track a position and orientation (e.g., a pose) of the imaging device 112, the robot 114 and/or robotic arm 116, and/or one or more surgical tools (or, more particularly, to track a pose of a navigated tracker attached, directly or indirectly, in fixed relation to the one or more of the foregoing). The navigation system 118 may include a display for displaying one or more images from an external source (e.g., the computing device 102, imaging device 112, or other source) or for displaying an image and/or video stream from the one or more cameras or other sensors of the navigation system 118.

In some implementations, the system 100 can operate without the use of the navigation system 118. The navigation system 118 may be configured to provide guidance to a surgeon or other user of the system 100 or a component thereof, to the robot 114, or to any other element of the system 100 regarding, for example, a pose of one or more anatomical elements, whether or not a tool is in the proper trajectory, and/or how to move a tool into the proper trajectory to carry out a surgical task according to a preoperative or other surgical plan.

The processor 104 may utilize data stored in memory 106 as a neural network. The neural network may include a machine learning architecture. In some aspects, the neural network may be or include one or more classifiers. In some other aspects, the neural network may be or include any machine learning network such as, for example, a deep learning network, a convolutional neural network, a reconstructive neural network, a generative adversarial neural network, or any other neural network capable of accomplishing functions of the computing device 102 described herein. Some elements stored in memory 106 may be described as or referred to as instructions or instruction sets, and some functions of the computing device 102 may be implemented using machine learning techniques.

For example, the processor 104 may support machine learning model(s) which may be trained and/or updated based on data (e.g., training data) provided or accessed by any of the computing device 102, the imaging device 112, the robot 114, the navigation system 118, the database 130, and/or the cloud network 134. The machine learning model(s) may be built and updated by the system 100 based on the training data (also referred to herein as training data and feedback).

In some examples, based on the data, the neural network may generate one or more algorithms (e.g., processing algorithms) supportive of object detection 129.

The database 130 may store information that correlates one coordinate system to another (e.g., imaging coordinate systems, robotic coordinate systems, a patient coordinate system, a navigation coordinate system, etc.). The database 130 may additionally or alternatively store, for example, one or more surgical plans (including, for example, pose information about a target and/or image information about a patient's anatomy at and/or proximate the surgical site, for use by the imaging device 112, robot 114, the navigation system 118, and/or a user of the computing device 102 or of the system 100); one or more images useful in connection with a surgery to be completed or analyzed; and/or any other useful information. The database 130 may additionally or alternatively store, for example, images captured or generated based on image data provided by the imaging device 112.

The database 130 may be configured to provide any such information to the computing device 102 or to any other device of the system 100 or external to the system 100, whether directly or via the cloud network 134. In some implementations, the database 130 may be or include part of a hospital image storage system, such as a picture archiving and communication system (PACS), a health information system (HIS), and/or another system for collecting, storing, managing, and/or transmitting electronic medical records including image data.

In some aspects, the computing device 102 may communicate with a server(s) and/or a database (e.g., database 130) directly or indirectly over a communications network (e.g., the cloud network 134). The communications network may include any type of known communication medium or collection of communication media and may use any type of protocols to transport data between endpoints. The communications network may include wired communications technologies, wireless communications technologies, or any combination thereof.

Wired communications technologies may include, for example, Ethernet-based wired local area network (LAN) connections using physical transmission mediums (e.g., coaxial cable, copper cable/wire, fiber-optic cable, etc.). Wireless communications technologies may include, for example, cellular or cellular data connections and protocols (e.g., digital cellular, personal communications service (PCS), cellular digital packet data (CDPD), general packet radio service (GPRS), enhanced data rates for global system for mobile communications (GSM) evolution (EDGE), code division multiple access (CDMA), single-carrier radio transmission technology (1×RTT), evolution-data optimized (EVDO), high speed packet access (HSPA), universal mobile telecommunications service (UMTS), 3G, long term evolution (LTE), 4G, and/or 5G, etc.), Bluetooth®, Bluetooth® low energy, Wi-Fi, radio, satellite, infrared connections, and/or ZigBee® communication protocols.

The Internet is an example of the communications network that constitutes an Internet Protocol (IP) network consisting of multiple computers, computing networks, and other communication devices located in multiple locations, and components in the communications network (e.g., computers, computing networks, communication devices) may be connected through one or more telephone systems and other means. Other examples of the communications network may include, without limitation, a standard Plain Old Telephone System (POTS), an Integrated Services Digital Network (ISDN), the Public Switched Telephone Network (PSTN), a Local Area Network (LAN), a Wide Area Network (WAN), a wireless LAN (WLAN), a Session Initiation Protocol (SIP) network, a Voice over Internet Protocol (VOIP) network, a cellular network, and any other type of packet-switched or circuit-switched network known in the art. In some cases, the communications network may include of any combination of networks or network types. In some aspects, the communications network may include any combination of communication mediums such as coaxial cable, copper cable/wire, fiber-optic cable, or antennas for communicating data (e.g., transmitting/receiving data).

The computing device 102 may be connected to the cloud network 134 via the communication interface 108, using a wired connection, a wireless connection, or both. In some implementations, the computing device 102 may communicate with the database 130 and/or an external device (e.g., a computing device) via the cloud network 134.

The system 100 or similar systems may be used, for example, to carry out one or more aspects of any of the methods 400, 600, 700, and/or 800 described herein. The system 100 or similar systems may also be used for other purposes.

Figure 1B:
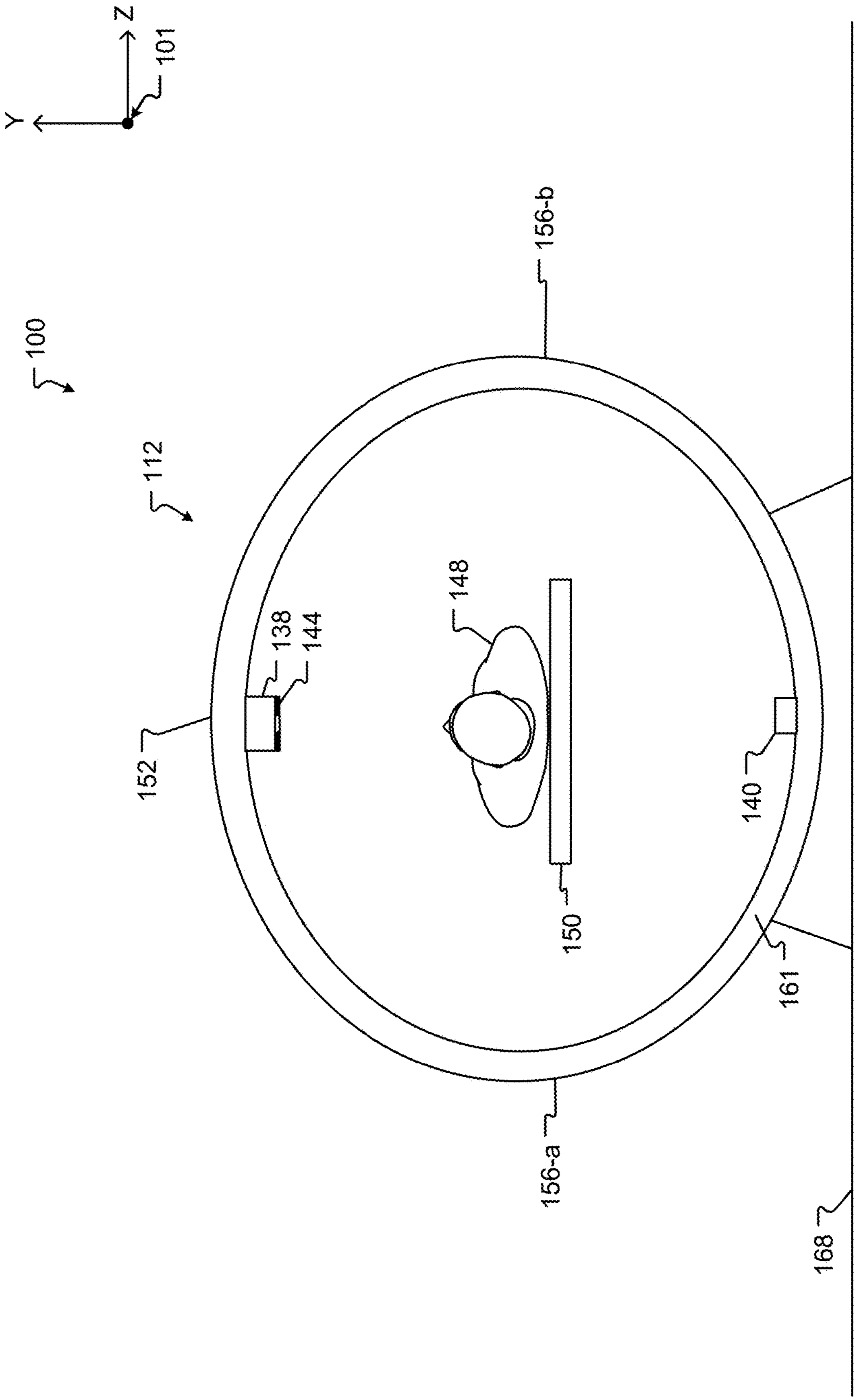

FIG. 1B illustrates an example of the system 100 that supports aspects of the present disclosure. FIG. 1C illustrates an example of the system 100 that supports aspects of the present disclosure. FIG. 1D illustrates an example of the system 100 that supports aspects of the present disclosure. Aspects of the system 100 previously described with reference to FIG. 1A and descriptions of like elements are omitted for brevity.

Figure 1C:
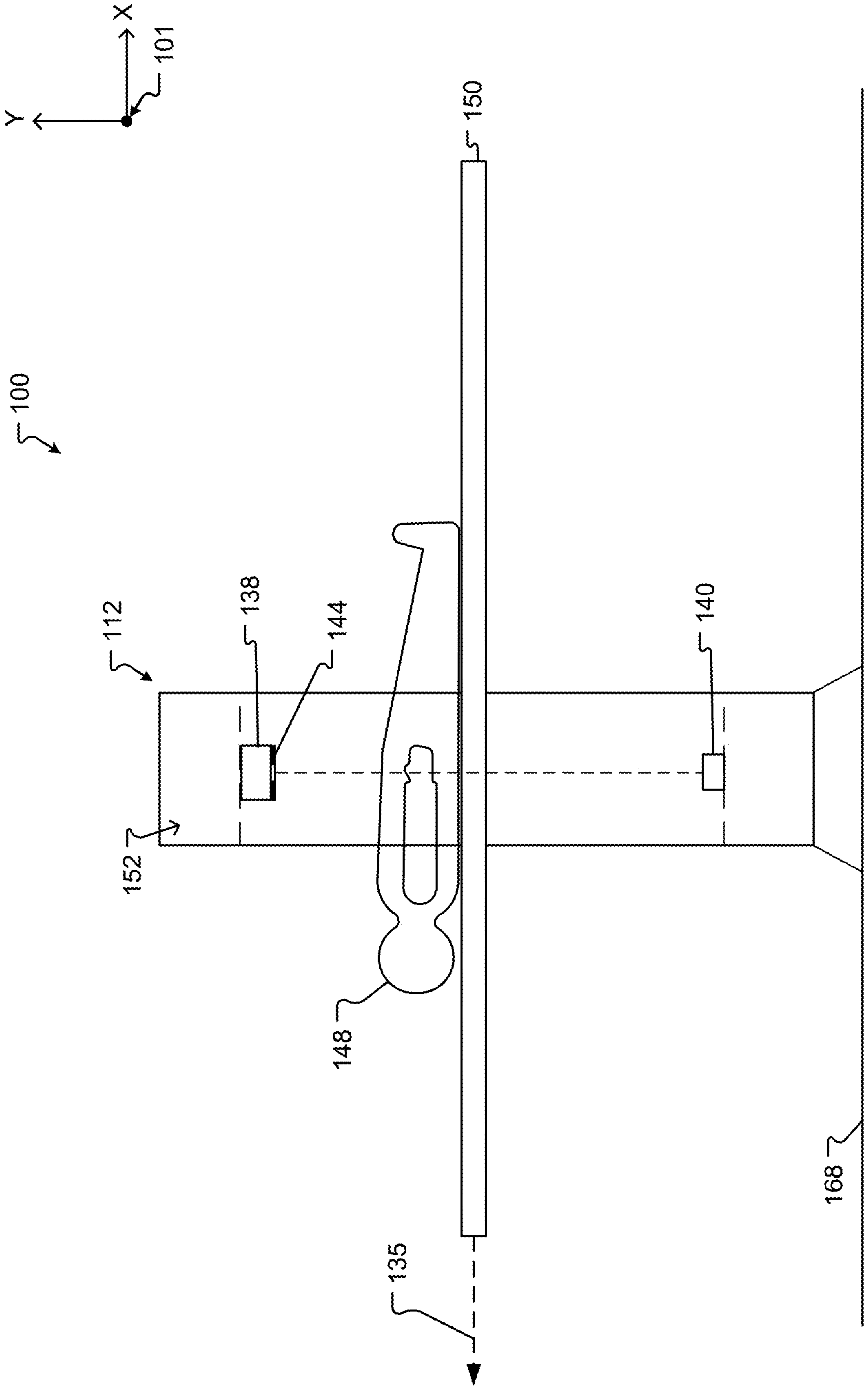
Figure 1D:
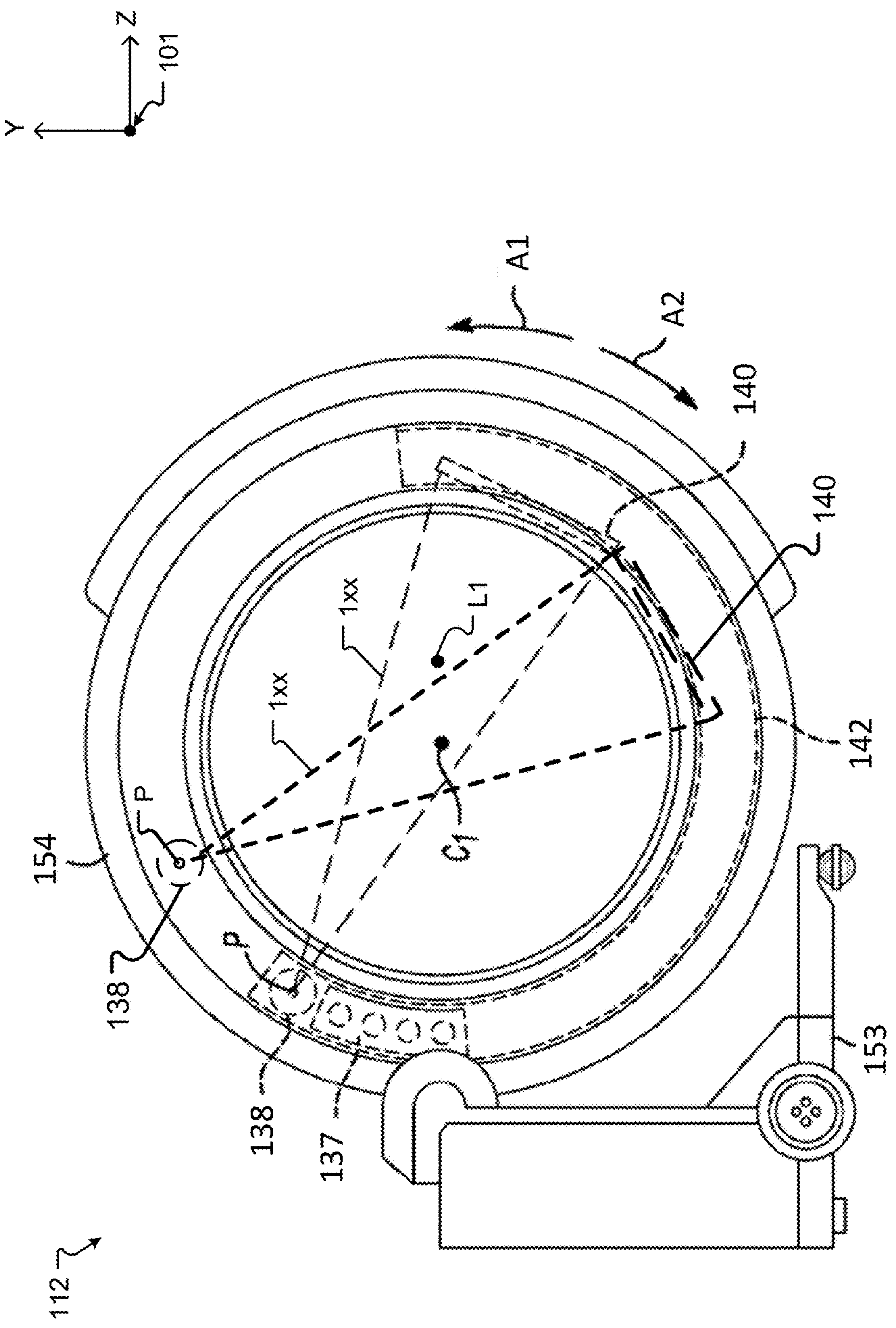

With reference to FIGS. 1B through 1D, features of the system 100 may be described in conjunction with a coordinate system 101. The coordinate system 101, as shown in FIGS. 1B, 1C, and 2A through 2D, includes three-dimensions including an X-axis, a Y-axis, and a Z-axis. Additionally or alternatively, the coordinate system 101 may be used to define planes (e.g., the XY-plane, the XZ-plane, and the YZ-plane) of the system 100. These planes may be disposed orthogonal, or at 90 degrees, to one another. While the origin of the coordinate system 101 may be placed at any point on or near the components of the system 100 (e.g., components of the imaging device 112, for the purposes of description, the axes of the coordinate system 101 are always disposed along the same directions from figure to figure, whether the coordinate system 101 is shown or not. In some examples, reference may be made to dimensions, angles, directions, relative positions, and/or movements associated with one or more components of the system 100 (e.g., imaging device 112) with respect to the coordinate system 101.

The system 100 may be used to initiate long scans of a patient, adjust imaging components to capture localization images of the patient, set or identify target coordinates associated with the localization images, perform a long scan process based on the localization images and the target coordinates, capture multidimensional images based on the target coordinates, and generating a long scan image based on the multidimensional images.

The imaging device 112 includes an upper wall or member 152, a lower wall 161 (also referred to herein as member 161), and a pair of sidewalls 156-*a* and 156-*b* (also referred to herein as members 156-*a* and 156-*b*). In some embodiments, the imaging device 112 is fixed securable to an operating room surface 168 (such as, for example, a ground surface of an operating room or other room). In other embodiments, the imaging device 112 may be releasably securable to the operating room wall 168 or may be a standalone component that is simply supported by the operating room wall 168.

A table 150 configured to support the patient 148 may be positioned orthogonally to the imaging device 112, such that the table 150 extends in a first direction from the imaging device 112. In some embodiments, the table 150 may be mounted to the imaging device 112. In other embodiments, the table 150 may be releasably mounted to the imaging device 112. In still other embodiments, the table 150 may not be attached to the imaging device 112. In such embodiments, the table 150 may be supported and/or mounted to an operating room wall, for example. In embodiments where the table 150 is mounted to the imaging device 112 (whether detachably mounted or permanently mounted), the table 150 may be mounted to the imaging device 112 such that a pose of the table 150 relative to the imaging device 112 is selectively adjustable. The patient 148 may be positioned on the table 150 in a supine position, a prone position, a recumbent position, and the like.

The table 150 may be any operating table configured to support the patient 148 during a surgical procedure. The table 150 may include any accessories mounted to or otherwise coupled to the table 150 such as, for example, a bed rail, a bed rail adaptor, an arm rest, an extender, or the like. The table 150 may be stationary or may be operable to maneuver the patient 148 (e.g., the table 150 may be moveable). In some embodiments, the table 150 has two positioning degrees of freedom and one rotational degree of freedom, which allows positioning of the specific anatomy of the patient anywhere in space (within a volume defined by the limits of movement of the table 150). For example, the table 150 may slide forward and backward and from side to side, tilt (e.g., around an axis positioned between the head and foot of the table 150 and extending from one side of the table 150 to the other) and/or roll (e.g., around an axis positioned between the two sides of the table 150 and extending from the head of the table 150 to the foot thereof). In other embodiments, the table 150 may be bendable at one or more areas (which bending may be possible due to, for example, the use of a flexible surface for the table 150, or by physically separating one portion of the table 150 from another portion of the table 150 and moving the two portions independently). In at least some embodiments, the table 150 may be manually moved or manipulated by, for example, a surgeon or other user, or the table 150 may include one or more motors, actuators, and/or other mechanisms configured to enable movement and/or manipulation of the table 150 by a processor such as a processor 104 of the computing device 102.

The imaging device 112 includes a gantry. The gantry may be or include a substantially circular, or "O-shaped," housing that enables imaging of objects placed into an isocenter thereof. In other words, the gantry may be positioned around the object being imaged. In some embodiments, the gantry may be disposed at least partially within the member 152, the sidewall 156-*a*, the sidewall 156-*b*, and the lower wall 161 of the imaging device 112.

The imaging device 112 also includes a source 138 and a detector 140. The source 138 may be a device configured to generate and emit radiation, and the detector 140 may be a device configured to detect the emitted radiation. In some embodiments, the source 138 and the detector 140 may be or include an imaging source and an imaging detector (e.g., the source 138 and the detector 140 are used to generate data useful for producing images). The source 138 may be positioned in a first position and the detector 140 may be positioned in a second position opposite the source 138. In some embodiments, the source 138 may include an X-ray source (e.g., a thermionic emission tube, a cold emission x-ray tube, or the like). The source 138 may project a radiation beam that passes through the patient 148 and onto the detector 140 located on the opposite side of the imaging device 112. The detector 140 may be or include one or more sensors that receive the radiation beam (e.g., once the radiation beam has passed through the patient 148) and transmit information related to the radiation beam to one or more other components (e.g., processor 104) of the system 100 for processing.

In some embodiments, the detector 140 may include an array. For example, the detector 140 may include three 2D flat panel solid-state detectors arranged side-by-side, and angled to approximate the curvature of the imaging device 112. It will be understood, however, that various detectors and detector arrays can be used with the imaging device 112, including any detector configurations used in typical diagnostic fan-beam or cone-beam CT scanners. For example, the detector 140 may include a 2D thin-film transistor X-ray detector using scintillator amorphous-silicon technology.

The source 138 may be or include a radiation tube (e.g., an x-ray tube) capable of generating the radiation beam. In some embodiments, the source 138 and/or the detector 140 may include a collimator 144 configured to confine or shape the radiation beam emitted from the source 138 and received at the detector 140. Once the radiation beam passes through patient tissue and received at the detector 140, the signals output from the detector 140 may be processed by the processor 104 to generate a reconstructed image of the patient tissue. In this way, the imaging device 112 can effectively generate reconstructed images of the patient tissue imaged by the source 138 and the detector 140.

The source 138 and the detector 140 may be attached to the gantry and configured to rotate 360 degrees around the patient 148 in a continuous or step-wise manner so that the radiation beam can be projected through the patient 148 at various angles. In other words, the source 138 and the detector 140 may rotate, spin, or otherwise revolve about an axis that passes through the top and bottom of the patient 148, with the patient anatomy that is the subject of the imaging positioned at the isocenter of the imaging device 112. The rotation may occur through a drive mechanism that causes the gantry to move such that the source 138 and the detector 140 encircle the patient 148 on the table 150.

At each projection angle, the radiation beam passes through and is attenuated by the patient 148. The attenuated radiation is then detected by the detector 140. The detected radiation from each of the projection angles can then be processed, using various reconstruction techniques, to produce a 2D or 3D reconstruction image of the patient 148. For example, the processor 104 may be used to perform image processing 120 to generate the reconstruction image. Additionally or alternatively, the source 138 and the detector 140 may move along a length of the patient 148, as depicted in FIG. 1B. For example, the table 150 holding the patient 148 may move in the direction of arrow 135 while the source 138 and detector 140 remain in a fixed location, such that the length of the patient can be scanned. In such embodiments, the scanned data may be used to generate one or more reconstructed images of the patient 148 and/or a long scan image of the patient 148.

The imaging device 112 may be included in the O-Arm® imaging system sold by Medtronic Navigation, Inc. having a place of business in Louisville, Colo., USA. The imaging device 112, including the O-Arm® imaging system, or other appropriate imaging systems supportive of aspects of the present disclosure can be found in U.S. Pat. Nos. 7,188,998, 7,108,421, 7,106,825, 7,001,045 and 6,940,941, each of which is incorporated herein by reference. The O-Arm® imaging system can include a mobile cart 153 (later illustrated at FIG. 1D) that supports movement of the imaging device 112 from one operating theater or room to another, and the gantry may move relative to the mobile cart 153.

In some example implementations, the system 100 may perform a long scan process by moving the source 138 and the detector 140 along a direction of an axis running through the patient 148. In some embodiments, the direction of the axis along which the source 138 and the detector 140 move may be the same direction as (e.g., extend in a direction parallel to) the direction indicated by the arrow 135. In some embodiments, the long scan process may include moving the patient 148 relative to the source 138 and the detector 140. For example, the patient 148 may be positioned in a prone position on the table 150. The system 100 may move the table 150 through an isocenter of the imaging device 112, in the direction (or opposite the direction) indicated by the arrow 135, such that the source 138 and the detector 140 generate projection data along a length of the patient 148.

In some embodiments, the system 100 may move the source 138 and the detector 140 relative to the patient 148 (or move the table 150 and patient 148 relative to the source 138 and the detector 140) at a predetermined rate and/or a fixed rate.

Referring to FIG. 1D, the imaging device 112 can include a tracking device 137 (e.g., an optical tracking device, an electromagnetic tracking device, etc.) to be tracked by the navigation system 118. The tracking device 137 can be associated directly with the source 138, the detector 140, rotor 142, the gantry 154, or other appropriate part of the imaging device 112 to determine the location or position of the source 138, detector 140, rotor 142, and/or gantry 154 relative to a selected reference frame. As illustrated, the tracking device 137 can be positioned on the exterior of the housing of the gantry 154. Accordingly, the imaging device 112 can be tracked relative to the patient 148 as can an instrument (not illustrated) in association with initial registration, automatic registration, or continued registration of the patient 148 relative to the image data.

With reference to FIG. 1D, the gantry 154 may define an isocenter of the imaging device 112. For example, a centerline Cl (represented as a dot on the ZY plane of the coordinate system 101) through the gantry 154 may define an isocenter or center of the imaging device 112, and any other line through the gantry 154, such as L1 (represented as a dot on the ZY plane of the coordinate system 101), may be considered to be off-isocenter or off-center of the imaging device 112. With reference to FIG. 1D, the patient 148 may be positioned along the centerline Cl of the gantry 154, such that a longitudinal axis (extending parallel to the X axis of the coordinate system 101) of the patient 148 is aligned with the isocenter of the imaging device 112. Image data acquired along the centerline Cl of the imaging device 112 may be considered isocenter or center image data, and image data acquired off-isocenter or off-center may be considered off-isocenter or off-center image data.

With reference to FIG. 1D, the source 138 may emit x-rays toward the patient 148, and the x-rays may pass through the patient and be detected by the detector 140. As is understood by one skilled in the art, the x-rays emitted by the source 138 may be emitted in a cone (a cone shape) and detected by the detector 140. The source 138 and the detector 140 may each be coupled to the rotor 142 so as to be generally diametrically opposed within the gantry 154, and movable within the gantry 154 about the patient 148. The detector 140 may move rotationally in a 360° motion around the patient 148 generally in the directions of arrows A1 and A2, and the source 138 may move in concert with the detector 140 such that the source 138 remains about 180° apart from and opposed to the detector 140.

The source 138 may be pivotably mounted to the rotor 142 and controlled by an actuator, such that the source 138 may be controllably pivoted about a focal spot P of the source 138 relative to the rotor 142 and the detector 140. By controllably pivoting the source 138, the system 100 may angle or alter the trajectory of the x-rays relative to the patient 148, without repositioning the patient 148 relative to the gantry 154. Further, the detector 140 may move about an arc relative to the rotor 142, in the direction of arrows A1 and A2. In one example, the detector 140 may pivot about the focal spot P of the source 138, such that the source 138 and detector 140 may pivot about the same angle. As the detector 140 may pivot at the same angle as the source 138, the detector 140 may detect the x-rays emitted by the source 138 at any desired pivot angle, which may enable the acquisition of off-center image data, examples of which will be discussed further herein. The rotor 142 may be rotatable about the gantry 154 in association with acquiring target image data (on center or off-center).

The system 100 may support a FOV preview feature and an interface supportive of patient orientation inputs. The FOV preview feature may be implemented at a user interface 110 (e.g., a display, a touchscreen display, etc.) of the system 100. In some aspects, via the FOV preview feature, the system 100 may provide users the ability to view a localization image 305 and select, on the localization image 305, crosshairs 330 to which the user wishes an imaging system to move. The system 100 may support user input of the crosshairs 330 via a user interface 110 (e.g., a touchscreen monitor displaying the localization image 305, a controller device, an audio input device, etc.) of the system 100. Example aspects of the FOV preview feature and automatic calculation of movement data based on user inputs (e.g., touch and go features) are described with reference to the following figures.

In some aspects, the system 100 may support an extended width mode of capture (also referred to herein as an ultra-wide mode of capture), which may include moving the source 138 and the detector 140 relative to the patient 148 in association with capturing multiple 2D localization images and generating, from the multiple 2D localization images, an extended localization image. In some aspects, the system 100 may support displaying the extended localization images via the FOV preview feature.

Figure 2A:
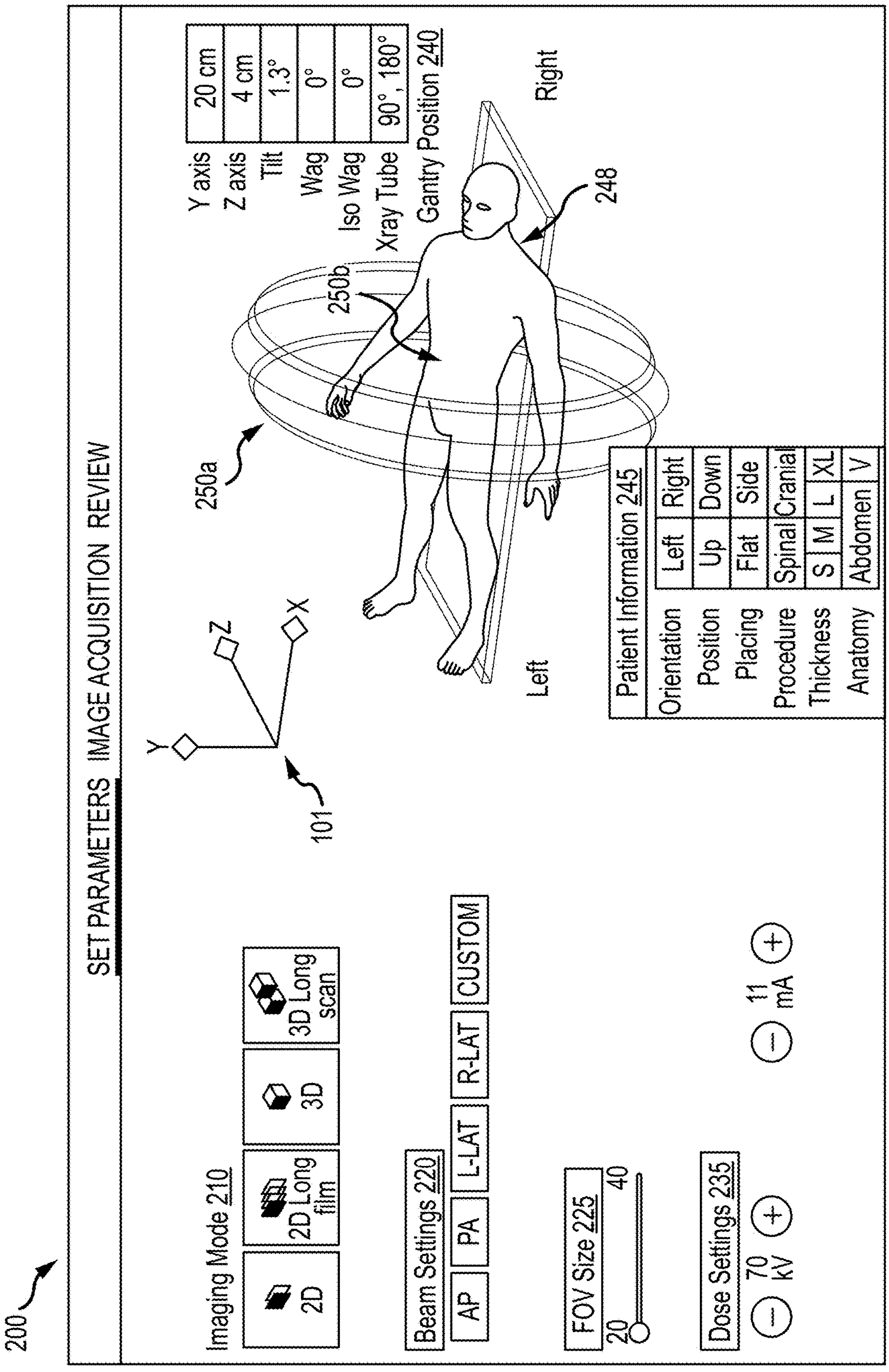
FIG. 2A illustrates an example of a user interface in accordance with aspects of the present disclosure.

FIG. 2A illustrates an example of a user interface 200 supported by the system 100 in accordance with aspects of the present disclosure.

The user interface 200 may include virtual interfaces (e.g., menus, buttons, sliders, etc.) that support setting parameters associated with scanning an anatomy of the patient 148. In some non-limiting examples, the virtual interfaces may support setting the parameters associated with an imaging mode 210, beam settings 220, FOV size 225, dose settings 235, gantry position 240, and patient information 245.

In some aspects, the user interface 200 may include a graphical indicator representative of a position of the source 138 and a graphical indicator 250-*a* (e.g., coloring, shading, boundaries, etc.) representative of a position of the rotor 142. In an example, graphical indicator 250-*a* may be indicated at the user interface 200 as a highlighted region of the ring around the patient GUI schematic 248. In some aspects, the system 100 may display, at the user interface 200, an indicator 250-*b* (e.g., a coloring, shading, etc.) corresponding to a region of the patient 148 to be scanned by the imaging device 112.

The system 100 may display, at the user interface 200, a patient GUI schematic 248. In some examples, the system 100 may display the patient GUI schematic 248 such that a pose of the patient GUI schematic 248 matches a pose of the patient 148.

An example of setting the position of the source 138 is described herein. In the example, the patient 148 may be laying in a supine position on the table 150, oriented towards the right. In an example, the user may select AP and L-LAT at beam settings 220 in association with a target acquisition view. The user may input patient orientation information at patient information 245. Under patient information 245 in the example of FIG. 2A, Orientation is 'Right', Position is 'Up', Placing is 'Flat', Procedure is 'Spinal', Thickness is 'M', and Anatomy is 'Abdomen'.

If the user selects 90 and 180 degrees at gantry position 240, the system 100 may display the patient GUI schematic 248 such that the patient GUI schematic 248 is in a prone position that matches the patient orientation information. Under gantry position 240 in the example of FIG. 2A, Y axis is '20 cm', Z axis is '4 cm', Tilt is '1.3°', Wag is '0°', Iso Wag is '0°', and Xray Tube is '90°, 180°'. In response to user selection of AP at beam settings 220, the system 100 display graphical indicator 250-*a* to indicate the corresponding source position for the source 138 and the corresponding position of the rotor 142. In some aspects, the system 100 may populate remaining rotor positions for PA, R-LAT, and L-LAT.

The system 100 may support updating the user interface 200 to match parameters as set in association with scanning the anatomy of the patient 148. For example, based on setting or modifying the patient information 245 (e.g., Orientation, Position, Placing, etc.), the system 100 may update the patient GUI schematic 248 based on the settings or modifications.

Aspects of the user interface 200 supported by the system 100 provide technical improvements of increased control of the source position, which may minimize radiation dose to an operator (e.g., radiology technician) based on proximity of the operator to the imaging device 112. As will be described herein, the system 100 and techniques described herein provide technical advantages of motion guidance for FOV preview workflow and displaying patient orientation overlays in acquired localization images of a patient 148.

Figure 2B:
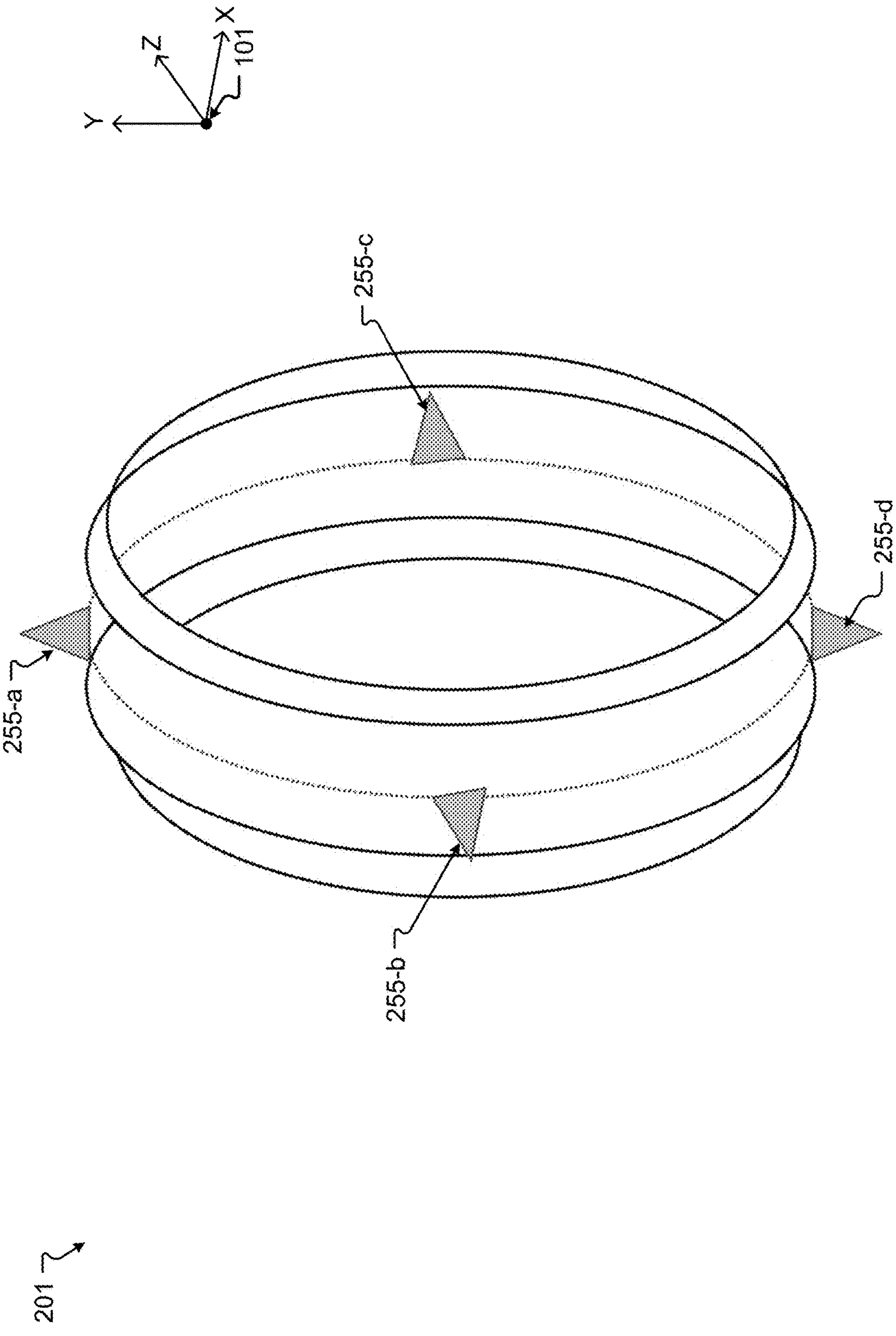
FIG. 2B illustrates an example of source positions of an imaging device in accordance with aspects of the present disclosure.

FIG. 2B illustrates an example 201 of source positions 255 (e.g., position 255-*a* through 255-d) of an imaging device 112 in accordance with aspects of the present disclosure.

Figure 3A:
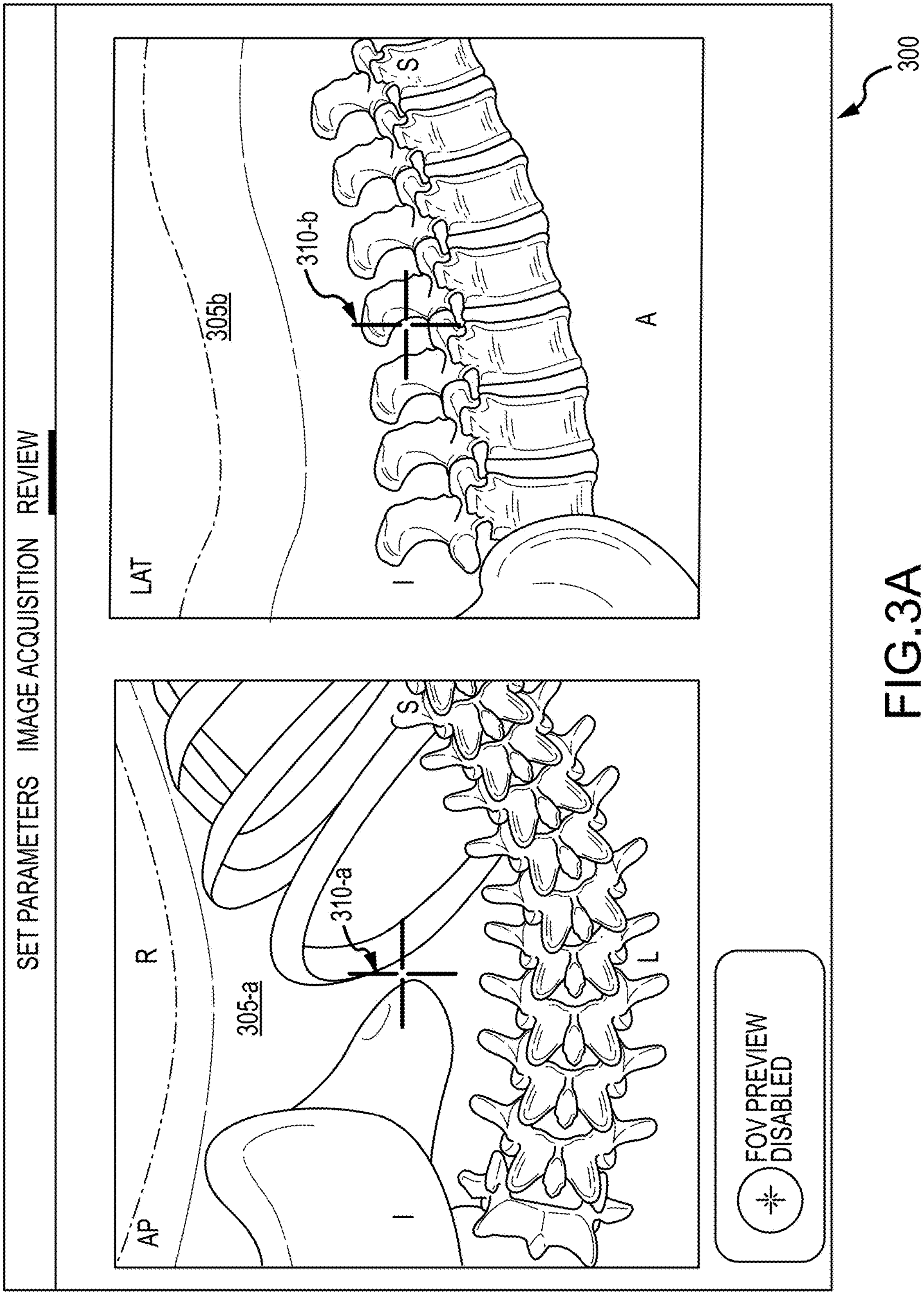
FIGS. 3A through 3C illustrate examples of a FOV preview in accordance with aspects of the present disclosure.
Figure 3B:
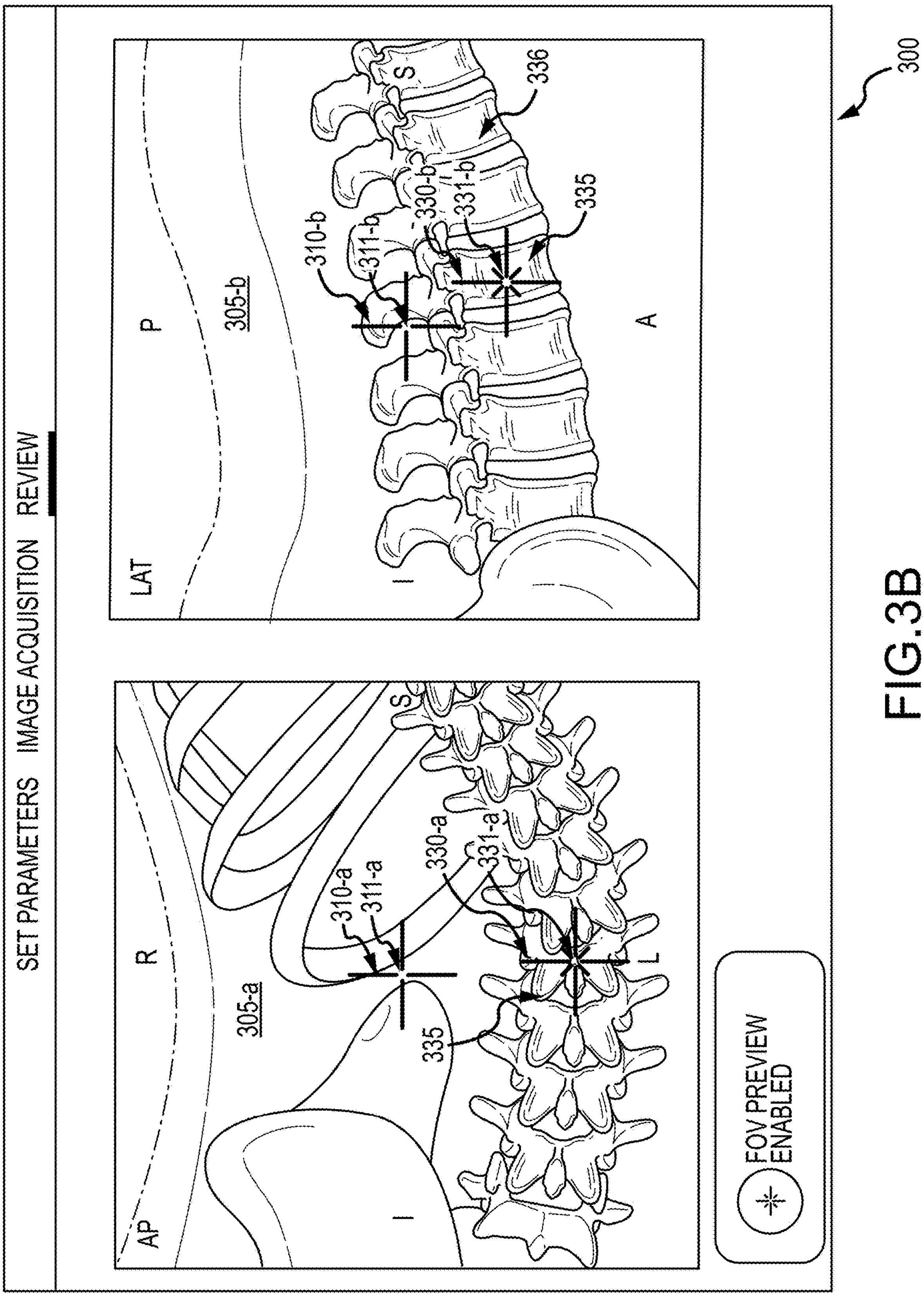
Figure 3C:
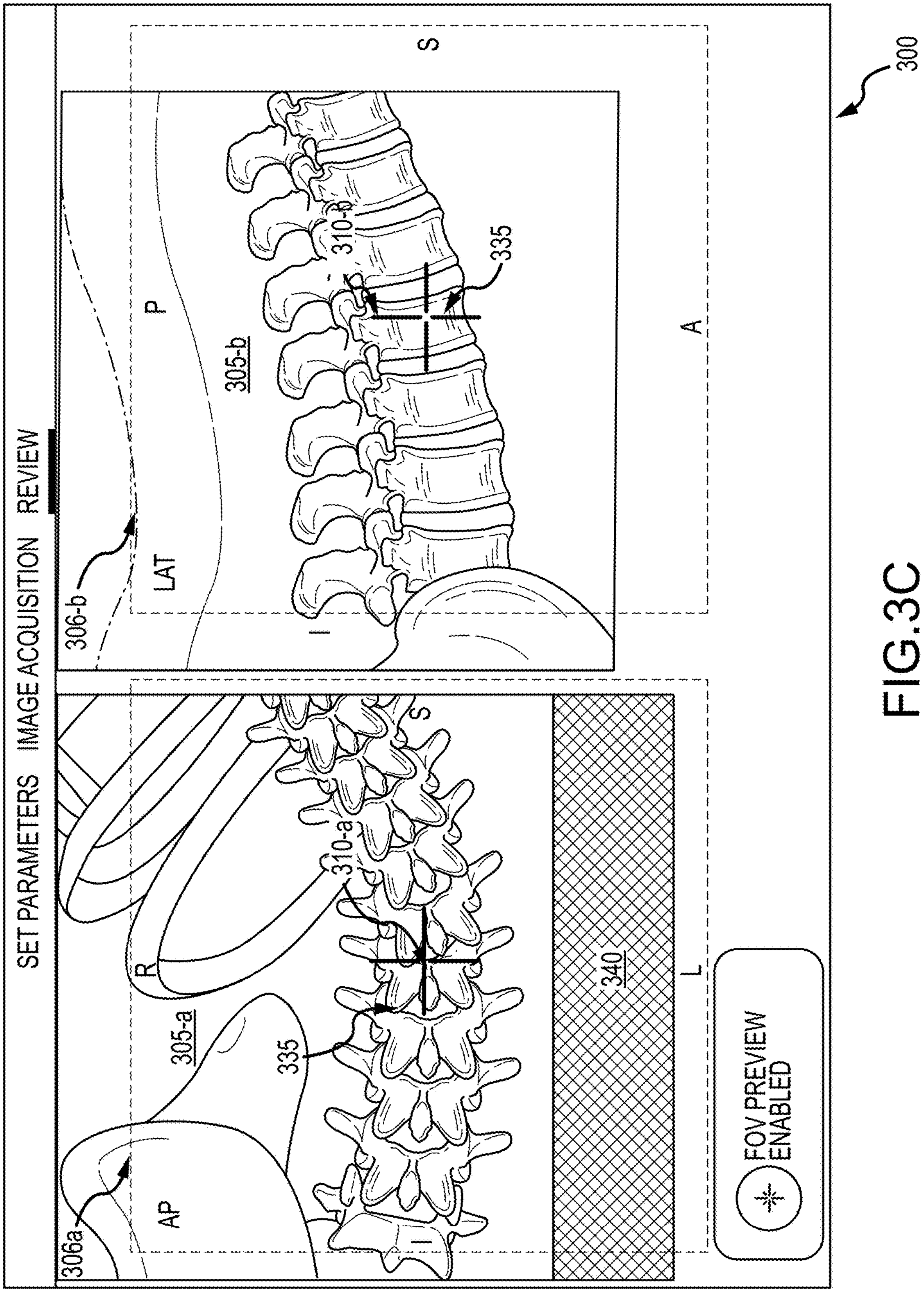

FIGS. 3A through 3C illustrate examples of a FOV preview 300 (also referred to herein as a FOV preview representation) supported by the system 100 in accordance with aspects of the present disclosure. As illustrated at FIGS. 3A through 3C, the system 100 may display one or more localization images 305 captured by the imaging device 112 via the FOV preview 300. Via the FOV preview 300, the system 100 may display localization images 305 of a patient 148 and related data, aspects of which are later described with reference to FIG. 4. In some non-limiting examples, the system 100 may display one or more control interfaces via the FOV preview 300.

As will be described with reference to FIGS. 1A through ID, FIG. 2A, FIGS. 3A through 3C, and FIG. 4, the system 100 may support a FOV preview 300 and an interface supportive of patient orientation inputs, via which a user may view a localization image 305. The system 100 may support user inputs for selecting, on the localization image 305, crosshairs 330 associated with desired movement of the imaging device 112. Aspects of the present disclosure support displaying any quantity of localization images 305 via the FOV preview 300 and performing a scan process based on user inputs via the FOV preview 300.

Figure 4:
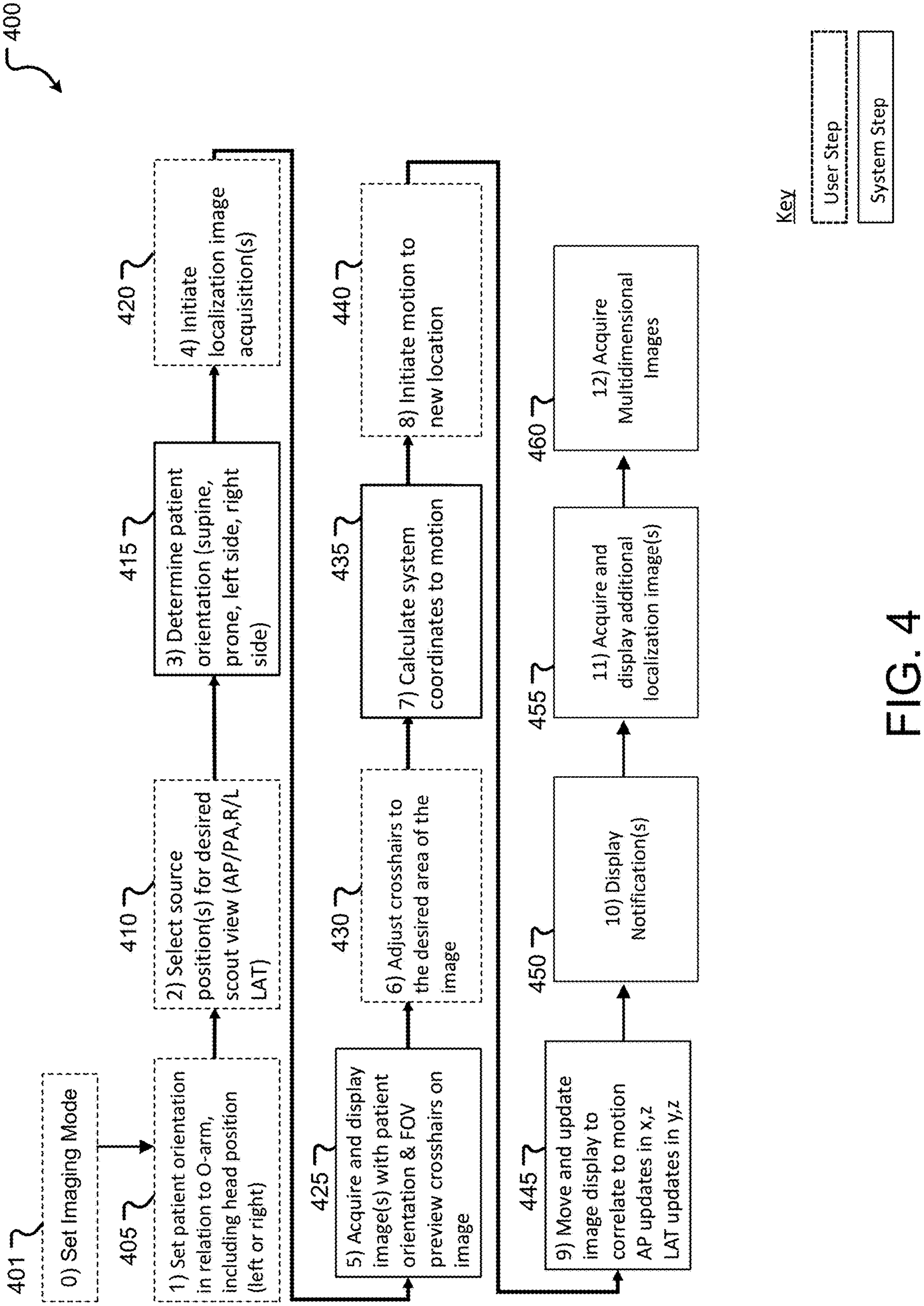
FIG. 4 illustrates an example of a process flow in accordance with aspects of the present disclosure.

FIG. 4 illustrates an example of a process flow 400 in accordance with aspects of the present disclosure.

Aspects of the process flow 400 may be implemented by the system 100 (as indicated by solid lines) and a user (as indicated by dotted lines). It is to be understood that although the process flow 400 is described as implemented by the system 100 (as indicated by solid lines) or a user (as indicated by dotted lines), aspects of the present disclosure are not limited thereto. For example, any aspects of the process flow 400 may be implemented by the system 100, a user, or both. It is to be understood that any device (e.g., computing device 102, imaging device 112, a robot 114, etc.) of the system 100 may perform the operations shown.

In the following description of the process flow 400, the operations may be performed in a different order than the order shown, or the operations may be performed in different orders or at different times. Certain operations may also be left out of the process flow 400, or other operations may be added to the process flow 400.

The process flow 400 is described herein with reference to FIGS. 1A through ID, FIG. 2A, and FIGS. 3A through 3C. In the example process flow 400, the imaging device 112 is an O-arm, but aspects of the present disclosure are not limited thereto.

At 401, the process flow 400 may include setting an imaging mode. The system 100 may support user selection of the imaging mode at imaging mode 210 (displayed at FOV preview 300). At the example illustrated at FIG. 2A, the selected imaging mode is '2D.'

At 405, the process flow 400 may include setting a patient 148 in relation to the imaging device 112. For example, the process flow 400 may include setting the head of the patient 148 in relation to the imaging device 112 (e.g., left or right). In an example, an operator or medical personnel may set or lay the patient 148 in relation to the imaging device 112 (or instruct the patient 148 accordingly). The operator or medical personnel may set patient orientation in relation to the imaging device 112 (e.g., O-arm), including head position (left or right).

The system 100 may support user selection of the orientation of the patient 148 at patient information 245. At the example illustrated at FIG. 2A, the selected orientation is 'Right.'

At 410, the process flow 400 may include selecting one or more source positions for a desired view (e.g., AP, PA, L-LAT, R-LAT, custom) associated with capturing a localization image 305. For example, the system 100 may support user selection of the one or more source positions via user interface 200 (e.g., at beam settings 220). At the example illustrated at FIG. 2A, the selected source positions include 'AP' (which corresponds to an AP view associated with the patient anatomy of the patient 148) and 'L-LAT' (which corresponds to a left LAT view associated with the patient anatomy of the patient 148).

The system 100 may support user selection of any quantity of source positions. For example, via the user interface 200, the user may select all desired localization images 305 (e.g., (e.g., AP image, PA image, L-LAT image, R-LAT image, a custom image, etc.) to be captured by the system 100.

At 415, the process flow 400 may include determining an orientation (e.g., supine, prone, left side, right side) of the patient 148. For example, the system 100 may identify one or more additional user entries with respect to patient information 245. At the example illustrated at FIG. 2A, based on the Orientation ('Right'), Position ('Up'), and Placing ('Flat'), the system 100 may determine that the orientation of the patient 148 is a supine position (i.e., lying on the back).

At 420, the process flow 400 may include initiating acquisition of one or more localization images 305. For example, the system 100 may support user inputs via the user interface 200 or a controller device (e.g., a pendant button of a controller) for initiating the acquisition of the one or more localization images 305. Accordingly, for example, the system 100 may provide the user with seamless acquisition of one or more localization images 305 based on target image orientation (e.g., AP, PA, R-LAT, L-LAT, etc.).

At 425, the process flow 400 may include acquiring and displaying captured localization images 305. For example, the system 100 may capture one or more localization images 305 based on the target image orientation and a target patient anatomy (e.g., Abdomen) (as selected at patient information 245 on the user interface 200).

The system 100 may display the image type of each localization image 305. The system 100 may display crosshairs 310 (also referred to herein as FOV preview crosshairs) on each localization image 305. In some examples, the crosshairs 310 may correspond to the isocenter of the imaging device 112. For example, each of the crosshairs 310-*a* and crosshairs 310-*b* may correspond to the isocenter of the imaging device 112.

In an example, for the localization image 305-*a* in FIG. 3A, the system 100 may indicate the localization image 305-*a* as an 'AP' image, display corresponding patient orientation information (e.g., I (inferior), S (superior), R (Right), and L (left)), and display crosshairs 310-*a*. In another example, for the localization image 305-*b*, the system 100 may indicate the localization image 305-*b* as a 'LAT' image, display patient orientation information (e.g., I (inferior), S (superior), P (Posterior), and A (Anterior)), and display crosshairs 310-*b*.

At 430, the process flow 400 may include adjusting the crosshairs 310 to a target area (e.g., a user desired area) of a localization image 305. In a non-limiting example, the process flow 400 may include centering the crosshairs 310 on the target area. The system 100 may support user inputs (e.g., touch inputs) via the user interface 200 or a controller device in association with centering the crosshairs 310.

For example, referring to FIG. 3B, the user may select target coordinates 331-*a* at localization image 305-*a* in association with aligning the crosshairs 310-*a* and the target coordinates 331-*a*. The target coordinates 331-*a* may correspond to a target portion 335 (e.g., a vertebra) of the patient anatomy. In an example, the system 100 may generate and display target crosshairs 330-*a* at the target coordinates 331-*a* in response to the user input.

In another example, the user may select target coordinates 331-*b* at localization image 305-*b* in association with aligning the crosshairs 310-*b* and the target coordinates 331-*b*. The target coordinates 331-*b* may correspond to the target portion 335 (e.g., vertebra) of the patient anatomy or a different target portion of the patient anatomy. In an example, the system 100 may generate and display target crosshairs 330-*b* at the target coordinates 331-*a* in response to the user input.

In some aspects, the system 100 may display the target crosshairs 330-*a* and target crosshairs 330-*b* as landmarks associated with tracking the target portion 335 in the FOV preview 300.

The system 100 may support the selection of different areas of interest respective to the localization images 305. For example, the system 100 may support a user input selecting the target portion 335 at the localization image 305-*a* and a second user input selecting the target portion 335 (or a different portion of the patient anatomy, for example, portion 336) at the localization image 305-*b*.

At 435, the process flow 400 may include calculating coordinates (also referred to herein as system coordinates) for positioning components associated with the system 100 (e.g., the gantry 154, wheels of the mobile cart 153, components of the imaging device 112, etc.) based on one or more target crosshairs 330. At 435, the process flow 400 may include calculating movement data (also referred to herein as motion data) based on the system coordinates.

For example, referring to localization image 305-*a* of FIG. 3B, the system 100 may calculate distance information and trajectory information between target coordinates 331-*a* (corresponding to a center of the target crosshairs 330-*a*) and coordinates 311-*a* (corresponding to a center of the crosshairs 310-*a*). Based on the distance information and trajectory information, the system 100 may calculate the system coordinates for positioning the imaging device 112 (e.g., for positioning the gantry 154) such that the target portion 335 will be aligned with the crosshairs 310-*a* at the localization image 305-*a*.

In another example, referring to localization image 305-*b* of FIG. 3B, the system 100 may calculate distance information and trajectory information between target coordinates 331-*b* (corresponding to a center of the target crosshairs 330-*b*) and coordinates 311-*b* (corresponding to a center of the crosshairs 310-*b*). Based on the distance information and trajectory information, the system 100 may calculate the system coordinates for positioning the imaging device 112 (e.g., for positioning the source 138, detector 140, rotor 142, and/or gantry 154) such that the target portion 335 will be aligned with the crosshairs 310-*b* at the localization image 305-*b*.

At 440, the process flow 400 may include initiating motion of the imaging device 112 (e.g., source 138, detector 140, rotor 142, and/or gantry 154) to a new location. According to example aspects of the present disclosure, the system 100 may support automatic, semi-automatic, and manual movement of the imaging device 112.

For example, the system 100 may support user inputs (e.g., touch inputs) at user interface 110 (e.g., at the FOV preview 300) and/or user inputs via a controller device in association with instructing the system 100 to position or move the imaging device 112. In an example, the system 100 may display a notification (not illustrated) via the user interface 110 for initiating motion of the imaging device 112 (e.g., source 138, detector 140, rotor 142, and/or gantry 154) to the new location. In an example, in response to a user input via the user interface 110 (e.g., a user confirmation at the FOV preview 300) or the controller device, the system 100 may automatically control the movement based on the movement data.

In the example case of a single localization image 305 (e.g., localization image 305-*a*), in response to a user input via virtual button 351 or the controller device, the system 100 may position the imaging device 112 based on system coordinates such that the target portion 335 (and crosshairs 330-*a*) will be aligned with the crosshairs 310-*a* at the localization image 305-*a*. In the example case of multiple localization images 305 (e.g., localization image 305-*a* and localization image 305-*b*), in response to a user input via virtual button 351 or the controller device, the system 100 may position the imaging device 112 based on system coordinates such that the target portion 335 (and crosshairs 330-*a*) will be aligned with the crosshairs 310-*a* at the localization image 305-*a*, and further, such that the target portion 335 (and target crosshairs 330-*b*) will be aligned with the crosshairs 310-*b* at the localization image 305-*b*.

In some aspects, the system 100 may support manual movement of the imaging device 112 by the user (e.g., via the user interface 200 or the controller device) in combination with guidance information associated with the positioning or orienting the imaging device 112 (e.g., source 138, detector 140, rotor 142, and/or gantry 154). In an example, the system 100 may generate and display the guidance information based on the movement data calculated at 435. In some aspects, the guidance information may include the movement data, target spatial coordinates for positioning the imaging device 112, directional prompts, or a combination thereof. In some aspects, the system 100 may provide any combination of visual, audible, and haptic prompts (e.g., via user interface 110, FOV preview 300, etc.) for providing the guidance information to a user.

In some aspects, the system 100 may support locking adjustments to one view at a time. For example, the system 100 may purposefully lock adjustments to a single axis of motion to assist user in repositioning the imaging device 112. For example, in response to detecting an active user input (e.g., via a controller device or user interface 110) in association with a first axis of motion (e.g., 'down' associated with 'Up/Down'), the system 100 may lock adjustments associated with other axes of motion (e.g., '4-way', 'Wag', 'Tilt', 'Isowag') until detecting completion of the active user input.

Accordingly, for example, the system 100 may support user controlled movement associated with positioning one or more components of the imaging device 112. It is to be understood that references to positioning, orienting, or moving the imaging device 112 may include positioning, orienting, or moving any component (e.g., source 138, detector 140, rotor 142, mobile cart 153, gantry 154, etc.) associated with the imaging device 112 and positioning, orienting, or moving other components (e.g., the table 150) associated with the system 100.

At 445, the process flow 400 may include moving and updating the image display to correlate to motion. For example, referring to FIG. 3C, the system 100 may reposition the localization images 305 in the FOV preview 300 based on the gantry coordinates (calculated at 435) and in response to movement of the imaging device 112 (as described with reference to 440).

In the example case of a single localization image 305 (e.g., localization image 305-*a*), the system 100 may position or move the localization image 305-*a* in correlation with the movement of the imaging device 112 described with reference to 440. For example, the system 100 may position or move the localization image 305-*a* such that the target crosshairs 330-*a* (previously illustrated at FIG. 3B) and corresponding target portion 335 are aligned with the crosshairs 310-*a*. In an example, the system 100 may position or move the localization image 305-*a* such that the positioning or movement corresponds to movement in the X-axis and Y-axis of a coordinate system of the imaging device 112 (or of the coordinate system 101).

In the example case of a multiple localization images 305 (e.g., localization image 305-*a* and localization image 305-*b*), the system 100 may further position or move the localization image 305-*b* in correlation with the movement of the imaging device 112 described with reference to 440. For example, the system 100 may position or move the localization image 305-*b* such that the target crosshairs 330-*b* (previously illustrated at FIG. 3B) and corresponding target portion 335 are aligned with the crosshairs 310-*b*. In an example, the system 100 may position or move the localization image 305-*b* such that the positioning or movement corresponds to movement in the Y-axis and Z-axis of the coordinate system of the imaging device 112 (or of the coordinate system 101).

At 450, the process flow 400 may include displaying a notification indicating whether target coordinates 330 (and target portion 335) associated with a localization image 305 are aligned with the isocenter of the imaging device 112. For example, in the example case of a single localization image 305 (e.g., localization image 305-*a*), the notification may indicate whether the target crosshairs 330-*a* (previously illustrated at FIG. 3B) and corresponding target portion 335 are aligned with the crosshairs 310-*a*.

Additionally, or alternatively, in the example case of a multiple localization images 305 (e.g., localization image 305-*a* and localization image 305-*b*), the notification may further indicate whether the target crosshairs 330-*b* (previously illustrated at FIG. 3B) and corresponding target portion 335 are aligned with the crosshairs 310-*b*.

In an example, the notification may include an icon and/or a message indicating alignment with the isocenter of the imaging device 112.

Additionally, or alternatively, at 450, the process flow 400 may include displaying a notification supportive of capturing and displaying one or more additional localization images 305. For example, the notification may include an instructional message associated with capturing one or more localization images 305: Additionally, or alternatively, the system 100 may display a virtual button at the FOV preview 300 for capturing and displaying one or more additional localization images 305.

At 455, the system 100 may acquire and display one or more additional localization images 305 (not illustrated) after moving and updating the image display to correlate to motion. For example, in response to a user input at a controller device (e.g., remote control) or at the FOV preview 300, the system 100 may acquire an additional localization image 305 (not illustrated) of the same image type (e.g., AP view) as the localization image 305-*a*. In an example, boundaries of the additional localization image 305 may correspond to a target imaging region 306-*a* illustrated at FIG. 3C and may further include a region 340 which was not captured in the localization image 305-*a*.

Additionally, or alternatively, the system 100 may acquire an additional localization image 305 (not illustrated) of the same image type (e.g., LAT view) as the localization image 305-*b*. In an example, boundaries of the additional localization image 305 may correspond to the region 306-*b* illustrated at FIG. 3C and may further include a region(s) not acquired in the localization image 305-*b*.

In some cases, the system 100 may proceed to 460 in the absence of acquiring and displaying one or more additional localization images 305 (as described with reference to 455). For example, in some example implementations, the process flow 400 may be implemented without the features described with reference to 455.

In some example aspects, any of 401 through 455 of the process flow 400 may be referred to as a preview scan process. In some examples, 420 through 455 of the process flow 400 may be referred to as a preview scan process.

At 460, the system 100 may acquire one or more multi-dimensional images including at least the target portion 335 of the patient anatomy. For example, the system 100 may acquire one or more multidimensional images based on the target coordinates 331-*a* associated with localization image 305-*a* and/or the target coordinates 331-*b* associated with the localization image 305-*b*. The system 100 may acquire the one or more multidimensional images based on an imaging mode 210 (as described with reference to FIG. 2A) set by the user.

In an example implementation, the system 100 may acquire one or more 2D images (e.g., X-ray image) based on a 2D imaging mode.

In another example implementation, the system 100 may perform a 2D long scan process associated with scanning the patient anatomy based on a 2D long film imaging mode. In an example (not illustrated), the localization images 305 acquired at 425 of the process flow 400 may be of the same image type (e.g., AP view, LAT view, etc.), acquired at different locations with respect to the X-axis of the coordinate system 101. The system 100 may support setting target coordinates at each of the localization images 305, positioning/moving the imaging device 112 based on the target coordinates, and updating the image display based on movement data associated with positioning/moving of the imaging device 112 (as described with reference to 430 through 445). The system 100 may acquire multiple 2D images in association with a scan path including the target coordinates, and the system 100 may generate a long scan image including the 2D images.

In another example implementation, the system 100 may acquire a 3D image (e.g., CT scan) based on the 3D imaging mode. In an example, referring to FIGS. 3A through 3C, based on the target coordinates 331-*a* set with respect to localization image 305-*a* (e.g., AP view) and the target coordinates 331-*b* set with respect to localization image 305-*b* (e.g., LAT view), the system 100 may acquire multiple 2D images including the patient anatomy based on the target coordinates. The areas acquired in the 2D images may correspond to the regions 306 described with reference to FIG. 3C. The system 100 may generate the 3D image based on the image data of the multiple 2D images.

In another example implementation, the system 100 may perform a 3D long scan process associated with scanning the patient anatomy based on a 3D long scan imaging mode. For example, based on target coordinates associated with localization images, the system 100 may set a scan path for acquiring multiple 3D images in association with a scan path including the target coordinates. The system 100 may generate a 3D long scan image based on merging data of the 3D images.

As described herein, the system 100 supports user selection of target coordinates 331 (e.g., target centers) for a scanning process, system based positioning/movement of the imaging device 112 based on the target coordinates 331, and updating of the FOV preview 300 based on movement data associated with positioning/moving the imaging device 112. Accordingly, for example, by setting target coordinates 331 at a localization image 305, a user may set a desired center of a corresponding multidimensional image to be acquired in a subsequent scanning process (e.g., 2D image capture, 2D long film, 3D image volume capture, 3D long scan).

In some examples, the term "capturing an image" may include the physical process of taking a picture of an object (e.g., patient anatomy) using an imaging device 112. In the example case of X-ray imaging, the term "capturing an image" may refer to the process of using an X-ray detector (e.g., detector 140) to record the X-ray photons that pass through the body of patient 148 and generate an image on film or on a digital detector. In some examples, the term "acquiring an image" may include the broader process of obtaining an image, in which the process may include several steps such as positioning the patient, selecting settings associated with the imaging device 112, and processing image data provided by the imaging device 112 to produce a final image. In some cases, the term "acquiring an image" may include the interpretation of the image by a radiologist or other medical professional. However, in the context of the present disclosure, it is to be understood that the terms "capturing" and "acquiring" may be used interchangeably herein and may be used to reference the processes described herein of obtaining an image of a patient anatomy.

Aspects of the present disclosure as described herein may be implemented based on localization images 305 of any image type. For example, the localization images 305 may include localization images captured from any angle (e.g., any angle with respect to the patient 148) or any plane of orientation. Non-limiting examples of localization images include anterior-posterior images, lateral images, oblique images, axial images, coronal images, sagittal images, and the like.

Figure 5:
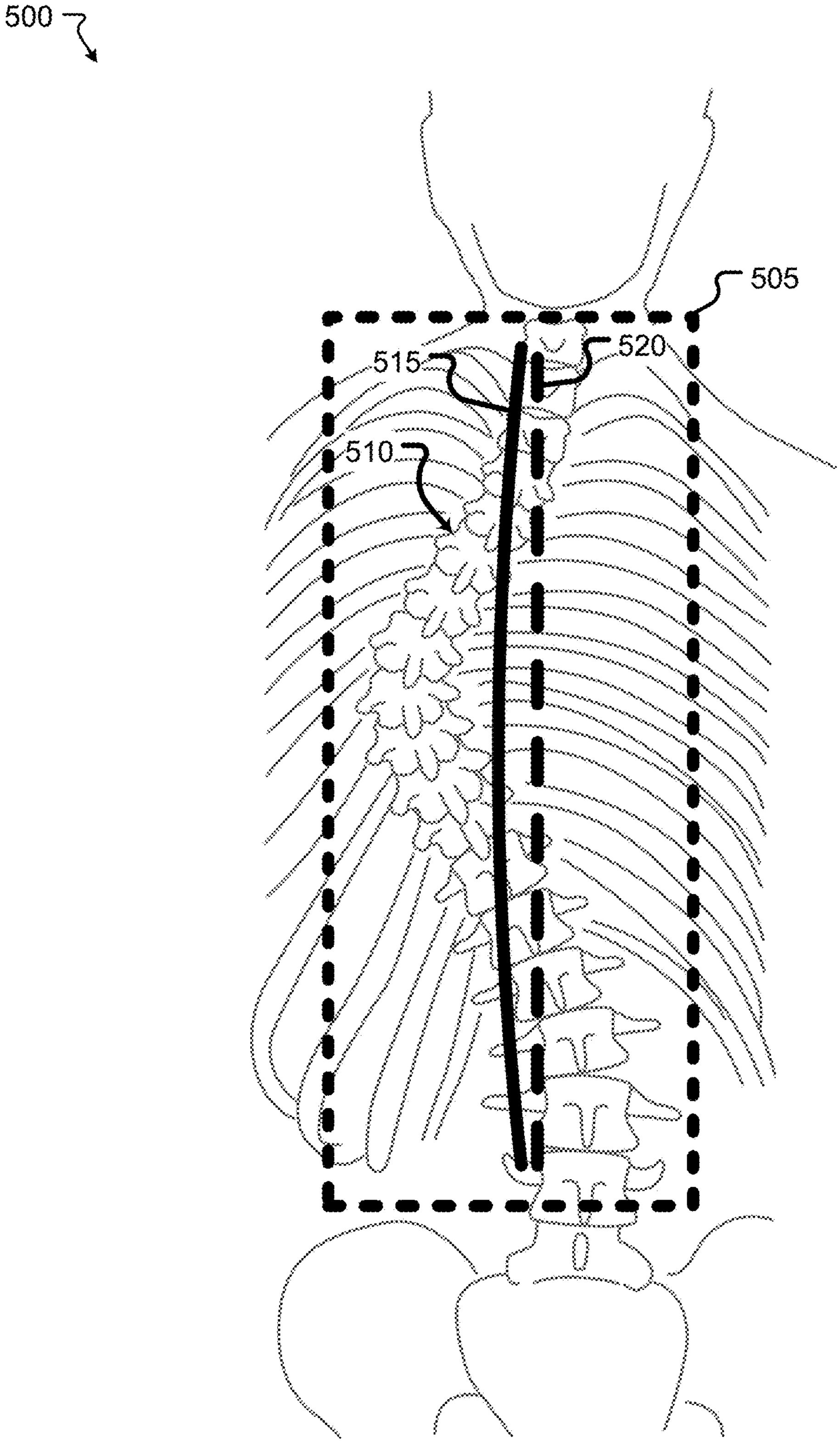
FIG. 5 illustrates an example of an image in accordance with aspects of the present disclosure.

FIG. 5 illustrates an example 500 of an image 505 supported by aspects of the present disclosure. The image 505 includes a patient anatomy 510 (e.g., a spinal structure), an implantable medical device 515 (e.g., a rod), and a graphical model 520 of the implantable medical device 515.

According to example aspects of the present disclosure, the system 100 supports to-scale representation using known pixel size of the image 505 to represent the pose of implantable medical device 515 relative to (e.g., at scale) the patient anatomy 510 for intraoperative planning and/or confirmation. For example, the system 100 supports representation of the to-scale pose of the implantable medical device 515 relative to actual size of the patient anatomy 510. Aspects of the present disclosure supportive of to-scale representation of the patient anatomy 510, implantable medical device 515, and graphical model 520 are described with reference to the process flow 600 of FIG. 6.

Figure 6:
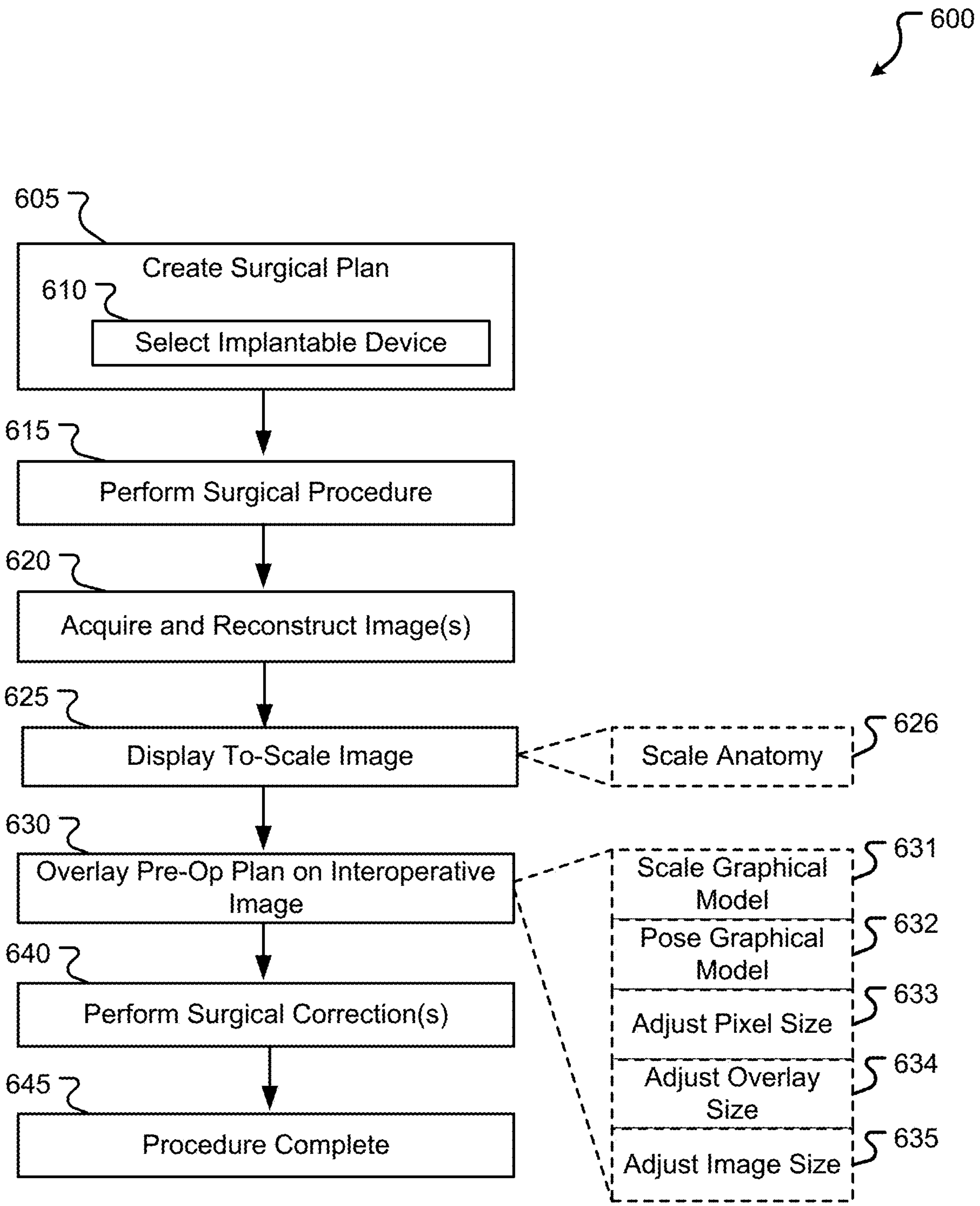
FIG. 6 illustrates an example of a process flow in accordance with aspects of the present disclosure.

FIG. 6 illustrates an example of a process flow 600 in accordance with aspects of the present disclosure. In some examples, process flow 600 may be implemented by aspects of the system 100 described herein.

In the following description of the process flow 600, the operations may be performed in a different order than the order shown, or the operations may be performed in different orders or at different times. Certain operations may also be left out of the process flow 600, or other operations may be added to the process flow 600.

It is to be understood that any device (e.g., computing device 102, imaging device 112, etc.) of the system 100 may perform the operations shown.

At 605, the process flow 600 may include creating a surgical plan (also referred to herein as a preoperative plan or a preoperative surgical plan). In an example, the system 100 may generate the surgical plan based on one or more user inputs. In another example, the system 100 may access or retrieve the surgical plan from a repository of surgical plans (e.g., at database 130).

At 610, the process flow 600 may include choosing an implantable medical device 515 associated with the surgical plan. In an example, the system 100 may identify a graphical model 520 of the implantable medical device 515 in response to a user input selecting the implantable medical device 515.

At 615, the process flow 600 may include performing a surgical procedure. For example, a user may perform the surgical procedure. In some cases, the user may perform the surgical procedure in combination with using the system 100 (e.g., imaging device 112, robot 114, navigation system 118, etc.).

At 620 of the process flow 600, the system 100 may acquire and reconstruct an image 505 with known pixel size and focal plane intraoperatively (e.g., during the surgical procedure). In the example of FIG. 5, the image 505 may be a 2D radiographic image (e.g., a 2D x-ray image). For example, the image 505 may be a 2D long scan image generated by the system 100 based on multiple localization images including the patient anatomy 510.

At 625, the process flow 600 may include displaying the image 505 on a digital display (e.g., user interface 110) associated with the system 100. The system 100 may display the image 505 at scale, such that the patient anatomy 510, surgical instruments, and the implantable medical device 515 are displayed at scale with respect to real-world dimensions thereof.

At 630, the process flow 600 may include overlaying the surgical plan on the image 505 to assess degree of completion of the surgical plan. For example, the system 100 may identify areas of overlap between the surgical plan and the patient anatomy 510. In some aspects, the surgical plan may include target pose information associated with the patient anatomy 510, and the system 100 may compare captured pose information of the patient anatomy 510 to the target pose information.

In some aspects, the surgical plan may include target pose information associated with the implantable medical device 515, and the system 100 may compare captured pose information of the implantable medical device 515 to the target pose information. In an example, the system 100 may display the graphical model 520 on the image 505 (e.g., overlaying the image 505) according to the target pose information for the implantable medical device 515.

The system 100 may support manual and software-based merger of the image 505 with the surgical plan. For example, the system 100 may merge image data associated with the image 505 with data of the surgical plan.

At 640, the process flow 600 may include performing one or more additional surgical corrections to meet alignment goals associated with the surgical plan. For example, a user may perform the one or more additional surgical corrections. In some cases, the user may perform the one or more additional surgical corrections in combination with using the system 100 (e.g., imaging device 112, robot 114, navigation system 118, etc.).

At 645, the process flow 600 may include marking the procedure as complete based on completion of the alignment goals. In an example, the system 100 may mark the procedure as complete in response to a user input. In another example, the system 100 may mark the procedure as complete based on a comparison of captured pose information of the patient anatomy 510 to the target pose information of the patient anatomy 510. In some other examples, the system 100 may mark the procedure as complete based on a comparison of captured pose information of the implantable medical device 515 to the target pose information of the implantable medical device 515.

According to example aspects of the present disclosure, the system 100 may support image scaling and object scaling. For example, at 626, the process flow 600 may include scaling the patient anatomy 510 captured in the image 505 to actual size of the patient anatomy 510. The system 100 may support scaling the image of the implantable medical device 515 as captured in the image 505 to actual size of the implantable medical device 515. In some examples, the system 100 may scale the patient anatomy 510 and the implantable medical device 515 as captured in the image 505 using the pixel size of the image 505.

The system 100 may support scaling the graphical model 520 of the implantable medical device 515 as overlaid on the implantable medical device 515. For example, at 631, the process flow 600 may include scaling the graphical model 520 using the pixel size of the image 505. Accordingly, for example, system 100 may support scaling the graphical model 520 of the implantable medical device 515 with respect to the patient anatomy 510 captured in the image 505.

The system 100 may support anatomical detection and labeling. For example, at 632, the process flow 600 may include identifying pre-existing anatomical labeling (e.g., T1, T2, L1, L2, etc.) of the patient anatomy 510 included in the image 505. In the example of a spinal structure, the process flow 600 may include detection and classification of the vertebral levels present in image 505. At 632, the process flow 600 may include posing the graphical model 520 on the image 505, based on the anatomical labeling. For example, the system 100 may automatically pose and match the graphical model 520 in coordination with the anatomical labeling of the patient anatomy 510.

Aspects of the present disclosure support automatic and/or manual (e.g., user input based) implementations of any portion of the process flow 600 described herein.

For example, the process flow 600 may support automated pixel size adjustment (at 633), automated overlay size adjustment (at 634), and automated image size adjustment (at 635) based on one or more criteria. In an example, the system 100 may detect that a threshold overlay value is exceeded between the surgical plan and the image 505. That is, for example, the system 100 may determine that an amount of overlap between the graphical model 520 and the implantable medical device 515 as captured in the image 505 exceeds a threshold value (e.g., the overlap between the graphical model 520 of the implantable medical device 515 and the image of the implantable medical device 515 as displayed in the image 505 is greater than the threshold value). In another example, the system 100 may determine that a size difference between the image of the patient anatomy 510 as captured in the image 505 and the patient anatomy 510 as represented in the surgical plan exceeds a threshold size value or threshold size ratio.

At 633, the system 100 may perform automatic refocusing with respect to image 505 to adjust or readjust the pixel size of the image 505. Additionally, or alternatively, at 634, the system 100 may adjust the size of the overlay of the surgical plan. Additionally, or alternatively, at 635, the system 100 may adjust the size of the image 505.

Accordingly, for example, the system 100 may adjust the pixel size (at 633), adjust the size of the overlay (at 634), and/or adjust the size of the image 505 (at 635) such that the graphical model 520 and the image of the implantable medical device 515 are substantially equal in size (e.g., a size difference between the graphical model 520 and the image of the implantable medical device 515 is less than the threshold value). The system 100 may adjust the pixel size (at 633), adjust the size of the overlay (at 634), and/or adjust the size of the image 505 (at 635) such that image of the patient anatomy 510 as captured in the image 505 is substantially equal in size to the patient anatomy 510 as represented in the surgical plan (e.g., a size difference between the image of patient anatomy 510 and the patient anatomy 510 as represented in the surgical plan is less than the threshold value).

Additionally, or alternatively, the system 100 may support user inputs associated with manually adjusting the pixel size (at 633), manually adjusting the size of the overlay (at 634), and/or manually adjusting the size of the image 505 (at 635) in association with scaling the image of the patient anatomy 510 as captured in the image 505 to the actual size of the patient anatomy 510.

As described herein, aspects of the process flow 600 support displaying a long scan image (e.g., image 505) having known pixel sizes such that the objects (e.g., patient anatomy 510, implantable medical device 515) captured in the long scan image are sized to scale with respect to the actual objects (e.g., CAD model representations of the objects).

Figure 7:
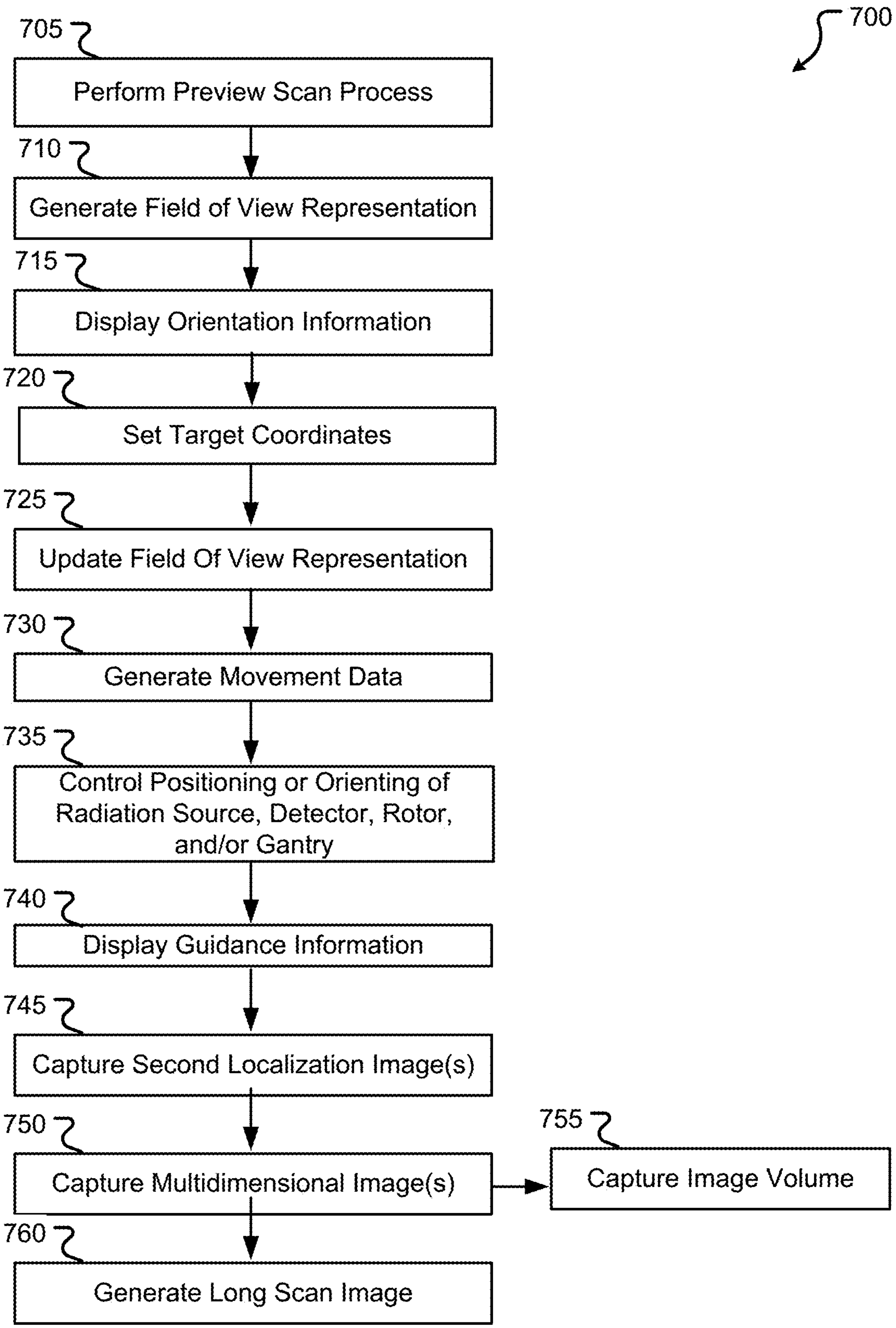
FIG. 7 illustrates an example of a process flow in accordance with aspects of the present disclosure.

FIG. 7 illustrates an example of a process flow 700 in accordance with aspects of the present disclosure.

In some examples, process flow 700 may be implemented by aspects of the system 100 described herein.

In the following description of the process flow 700, the operations may be performed in a different order than the order shown, the operations may be performed in different orders or at different times, or some operations may be performed in parallel. Certain operations may also be left out of the process flow 700, or other operations may be added to the process flow 700.

It is to be understood that any device (e.g., computing device 102, imaging device 112, etc.) of the system 100 may perform the operations shown.

Aspects of the process flow 700 may be implemented by an imaging system including: a processor coupled with the imaging system; and memory coupled with the processor and storing data thereon that, when executed by the processor, enable the processor to perform operations of the process flow 700.

At 705, the process flow 700 may include performing a preview scan process associated with scanning a patient anatomy, wherein performing the preview scan process includes capturing (or acquiring) one or more localization images including a portion of the patient anatomy.

In some examples, each of the one or more localization images may be: an anterior-posterior image, a posterior-anterior image, a lateral image, an oblique image, an axial image, a coronal image, or a sagittal image.

In some aspects, capturing (or acquiring) the one or more localization images is based on: one or more positions of a radiation source of the imaging system; and pose information of a subject with respect to the imaging system.

At 710, the process flow 700 may include generating a field of view representation of the patient anatomy including the one or more localization images.

At 715, the process flow 700 may include displaying orientation information associated with the patient anatomy and the one or more localization images.

At 720, the process flow 700 may include setting target coordinates associated with the one or more localization images in response to a user input associated with the imaging system. In some examples, the user input includes an input via at least one of: a display; a controller device; and an audio input device.

In some examples, the one or more localization images include a first localization image and a second localization image. The process flow 700 may include pausing setting of second target coordinates in association with the second localization image in response to detecting an active user input of setting first target coordinates in association with the first localization image. The process flow 700 may include enabling the setting of the second target coordinates in response to detecting completion of the active user input.

At 725, the process flow 700 may include updating the field of view representation based on the target coordinates.

At 730, the process flow 700 may include, based on the target coordinates, generating movement data associated with positioning or orienting at least one of a radiation source, a detector, a rotor, and a gantry of the imaging system in association with capturing (or acquiring) the one or more multidimensional images.

In some aspects, generating the movement data is based on: a pixel size associated with the one or more localization images; and a focal plane associated with the preview scan process.

At 735, the process flow 700 may include controlling the positioning or orienting of at least one of the radiation source, the detector, the rotor, and the gantry based on the movement data.

Additionally, or alternatively, at 740, the process flow 700 may include displaying guidance information associated with the positioning or orienting of at least one of the radiation source, the detector, the rotor, and the gantry based on the movement data.

In some examples, at 745, the process flow 700 may include capturing (or acquiring) one or more second localization images including the portion of the patient anatomy based on the target coordinates.

At 750, the process flow 700 may include capturing (or acquiring) one or more multidimensional images including at least the portion of the patient anatomy based on target coordinates associated with the one or more localization images.

In some aspects, the one or more localization images include: a first localization image of a first image type including the portion of the patient anatomy; and a second localization image of a second image type including the portion of the patient anatomy, wherein capturing (or acquiring) the one or more multidimensional images (at 750) is based on at least one of the first localization image and the second localization image.

In some aspects, capturing (or acquiring) the one or more multidimensional images is based on: the one or more second localization images; one or more second target coordinates associated with the one or more second localization images; or both (as described with reference to 745).

In some aspects, capturing (or acquiring) the one or more multidimensional images may include capturing (or acquiring) (at 755) an image volume including at least the portion of the patient anatomy based on image data of the one or more multidimensional images.

In some aspects, at 760, the process flow 700 may include generating a long scan image including at least the portion of the patient anatomy based on image data of the one or more multidimensional images.

Figure 8:
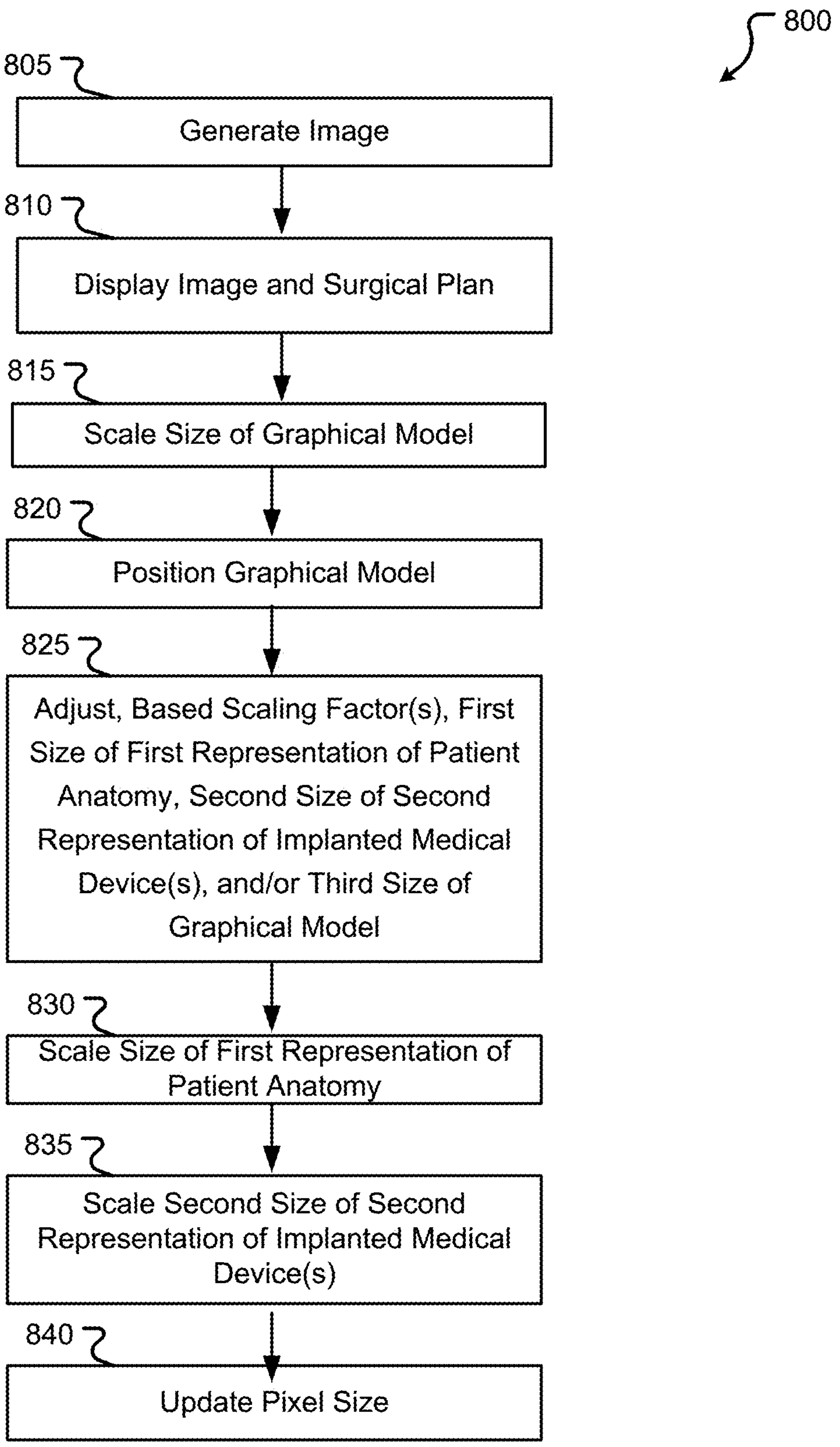
FIG. 8 illustrates an example of a process flow in accordance with aspects of the present disclosure.

FIG. 8 illustrates an example of a process flow 800 in accordance with aspects of the present disclosure.

In some examples, process flow 800 may be implemented by aspects of the system 100 described herein.

In the following description of the process flow 800, the operations may be performed in a different order than the order shown, the operations may be performed in different orders or at different times, or some operations may be performed in parallel. Certain operations may also be left out of the process flow 800, or other operations may be added to the process flow 800.

It is to be understood that any device (e.g., computing device 102, imaging device 112, etc.) of the system 100 may perform the operations shown.

Aspects of the process flow 800 may be implemented by an imaging system including: a processor coupled with the imaging system; and memory coupled with the processor and storing data thereon that, when executed by the processor, enable the processor to perform operations of the process flow 800.

At 805, the process flow 800 may include generating an image including a patient anatomy and one or more implanted medical devices based on performing a long scan process associated with scanning the patient anatomy. In some aspects, generating the image includes sizing a first representation of the patient anatomy and a second representation of the one or more implanted medical devices in the image based on: a pixel size associated with the image; and a focal plane associated with the long scan process.

In some aspects, the image includes a long scan image.

In some aspects, the image includes an X-ray image, a computed tomography (CT) image, or a magnetic resonance imaging (MRI) image.

At 810, the process flow 800 may include displaying the image and a surgical plan associated with the patient anatomy at a user interface of the imaging system, wherein displaying the image and the surgical plan includes at least partially overlaying the surgical plan over the image.

In some aspects, the surgical plan includes a graphical model of the one or more implanted medical devices; and displaying the image and the surgical plan includes displaying the graphical model in combination with at least one of: the first representation of the patient anatomy; and the second representation of the one or more implanted medical devices.

In some aspects, the surgical plan includes one or more preoperative images, one or more reference intraoperative images, or both. In some aspects, the image includes one or more second intraoperative images, one or more postoperative images, or both.

At 815, the process flow 800 may include scaling a size of the graphical model based on the pixel size associated with the image.

In some aspects, the surgical plan includes labeling information associated with the patient anatomy. At 820, the process flow 800 may include positioning the graphical model with respect to the first representation of the patient anatomy based on: the labeling information; and pixels corresponding to the patient anatomy from among a plurality of pixels associated with the image.

At 825, the process flow 800 may include adjusting, based on one or more scaling factors, at least one of: a first size of the first representation of the patient anatomy; a second size of the second representation of the one or more implanted medical devices; and a third size of the graphical model of the one or more implanted medical devices.

At 830, the process flow 800 may include scaling a size of the first representation of the patient anatomy with reference to a physical size of the patient anatomy in one or more dimensions.

At 835, the process flow 800 may include scaling a size of the second representation of the one or more implanted medical devices with reference to a physical size of the one or more implanted medical devices in one or more dimensions.

At 840, the process flow 800 may include updating a pixel size associated with the image based on a change in focus level associated with generating the image, wherein displaying the image is based on the updated pixel size.

As noted above, the present disclosure encompasses methods with fewer than all of the features identified in FIGS. 4, 6, 7, and 8 (and the corresponding description of the process flows 400, 600, 700, and 800), as well as methods that include additional features beyond those identified in FIGS. 4, 6, 7, and 8 (and the corresponding description of the process flows 400, 600, 700, and 800). The present disclosure also encompasses methods that include one or more steps from one method described herein, and one or more steps from another method described herein. Any correlation described herein may be or include a registration or any other correlation.

The foregoing is not intended to limit the disclosure to the form or forms disclosed herein. In the foregoing Detailed Description, for example, various features of the disclosure are grouped together in one or more aspects, implementations, and/or configurations for the purpose of streamlining the disclosure. The features of the aspects, implementations, and/or configurations of the disclosure may be combined in alternate aspects, implementations, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, implementation, and/or configuration. Thus, the following claims are hereby incorporated into this Detailed Description, with each claim standing on its own as a separate preferred implementation of the disclosure.

Moreover, though the foregoing has included description of one or more aspects, implementations, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, implementations, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

Example aspects of the present disclosure include:

An imaging system including: a processor coupled with the imaging system; and a memory storing instructions thereon that, when executed by the processor, cause the processor to: perform a preview scan process associated with scanning a patient anatomy, wherein performing the preview scan process includes capturing one or more localization images including a portion of the patient anatomy; and capture one or more multidimensional images including at least the portion of the patient anatomy based on target coordinates associated with the one or more localization images.

Any of the aspects herein, wherein the instructions are further executable by the processor to: based on the target coordinates, generate movement data associated with positioning or orienting at least one of a radiation source, a detector, a rotor, and a gantry of the imaging system in association with capturing the one or more multidimensional images.

Any of the aspects herein, wherein the instructions are further executable by the processor to: control the positioning or orienting of at least one of the radiation source, the detector, the rotor, and the gantry based on the movement data.

Any of the aspects herein, wherein the instructions are further executable by the processor to: display guidance information associated with the positioning or orienting of at least one of the radiation source, the detector, the rotor, and the gantry based on the movement data.

Any of the aspects herein, wherein generating the movement data is based on: a pixel size associated with the one or more localization images; and a focal plane associated with the preview scan process.

Any of the aspects herein, wherein the one or more localization images include: a first localization image of a first image type including the portion of the patient anatomy; and a second localization image of a second image type including the portion of the patient anatomy, wherein capturing the one or more multidimensional images is based on at least one of the first localization image and the second localization image.

Any of the aspects herein, wherein the instructions are further executable by the processor to: set the target coordinates in response to a user input associated with the imaging system.

Any of the aspects herein, wherein the user input includes an input via at least one of: a display; a controller device; and an audio input device.

Any of the aspects herein, wherein the instructions are further executable by the processor to: generate a field of view representation of the patient anatomy including the one or more localization images; and update the field of view representation based on the target coordinates.

Any of the aspects herein, wherein the instructions are further executable by the processor to: capture one or more second localization images including the portion of the patient anatomy based on the target coordinates, wherein capturing the one or more multidimensional images is based on: the one or more second localization images; one or more second target coordinates associated with the one or more second localization images; or both.

Any of the aspects herein, wherein the instructions executable to capture the one or more multidimensional images are further executable by the processor to capture an image volume including at least the portion of the patient anatomy based on image data of the one or more multidimensional images.

Any of the aspects herein, wherein the instructions are further executable by the processor to generate a long scan image including at least the portion of the patient anatomy based on image data of the one or more multidimensional images.

Any of the aspects herein, wherein each of the one or more localization images is: an anterior-posterior image, a posterior-anterior image, a lateral image, an oblique image, an axial image, a coronal image, or a sagittal image.

Any of the aspects herein, wherein capturing the one or more localization images is based on: one or more positions of a radiation source of the imaging system; and pose information of a subject with respect to the imaging system.

Any of the aspects herein, wherein the instructions are further executable by the processor to: display orientation information associated with the patient anatomy and the one or more localization images.

Any of the aspects herein, wherein: the one or more localization images include a first localization image and a second localization image; and the instructions are further executable by the processor to: pause setting of second target coordinates in association with the second localization image in response to detecting an active user input of setting first target coordinates in association with the first localization image; and enable the setting of the second target coordinates in response to detecting completion of the active user input.

A system including: a processor; and a memory storing instructions thereon that, when executed by the processor, cause the processor to: perform a preview scan process associated with scanning a patient anatomy, wherein performing the preview scan process includes capturing one or more localization images including a portion of the patient anatomy; and capture one or more multidimensional images including at least the portion of the patient anatomy based on target coordinates associated with the one or more localization images.

Any of the aspects herein, wherein the instructions are further executable by the processor to: based on the target coordinates, generate movement data associated with positioning or orienting at least one of a radiation source, a detector, a rotor, and a gantry of the system in association with capturing the one or more multidimensional images.

Any of the aspects herein, wherein the instructions are further executable by the processor to: control the positioning or orienting of at least one of the radiation source, the detector, the rotor, and the gantry based on the movement data; display guidance information associated with the positioning or orienting of at least one of the radiation source, the detector, the rotor, and the gantry based on the movement data; or a combination thereof.

In some aspects, the techniques described herein relate to a method including: performing, by an imaging system, a preview scan process associated with scanning a patient anatomy, wherein performing the preview scan process includes capturing one or more localization images including a portion of the patient anatomy; and capturing one or more multidimensional images including at least the portion of the patient anatomy based on target coordinates associated with the one or more localization images.

In some aspects, the techniques described herein relate to an imaging system including: a processor coupled with the imaging system; and a memory storing instructions thereon that, when executed by the processor, cause the processor to: generate an image including a patient anatomy and one or more implanted medical devices based on performing a long scan process associated with scanning the patient anatomy, wherein generating the image includes sizing a first representation of the patient anatomy and a second representation of the one or more implanted medical devices in the image based on: a pixel size associated with the image; and a focal plane associated with the long scan process; and display the image and a surgical plan associated with the patient anatomy at a user interface of the imaging system, wherein displaying the image and the surgical plan includes at least partially overlaying the surgical plan over the image.

Any of the aspects herein, wherein: the surgical plan includes a graphical model of the one or more implanted medical devices; and displaying the image and the surgical plan includes displaying the graphical model in combination with at least one of: the first representation of the patient anatomy; and the second representation of the one or more implanted medical devices.

Any of the aspects herein, wherein the instructions are further executable by the processor to: scale a size of the graphical model based on the pixel size associated with the image.

Any of the aspects herein, wherein: the surgical plan includes labeling information associated with the patient anatomy; and the instructions are further executable by the processor to position the graphical model with respect to the first representation of the patient anatomy based on: the labeling information; and pixels corresponding to the patient anatomy from among a plurality of pixels associated with the image.

Any of the aspects herein, wherein the instructions are further executable by the processor to adjust, based on one or more scaling factors, at least one of: a first size of the first representation of the patient anatomy; a second size of the second representation of the one or more implanted medical devices; and a third size of the graphical model of the one or more implanted medical devices.

Any of the aspects herein, wherein the image includes a long scan image.

Any of the aspects herein, wherein the instructions are further executable by the processor to: scale a size of the first representation of the patient anatomy with reference to a physical size of the patient anatomy in one or more dimensions.

Any of the aspects herein, wherein the instructions are further executable by the processor to: scale a size of the second representation of the one or more implanted medical devices with reference to a physical size of the one or more implanted medical devices in one or more dimensions.

Any of the aspects herein, wherein the instructions are further executable by the processor to: update a pixel size associated with the image based on a change in focus level associated with generating the image, wherein displaying the image is based on the updated pixel size.

Any of the aspects herein, wherein: the surgical plan includes one or more preoperative images, one or more reference intraoperative images, or both; and the image includes one or more second intraoperative images, one or more postoperative images, or both.

Any of the aspects herein, wherein the image includes an X-ray image, a computed tomography (CT) image, or a magnetic resonance imaging (MRI) image.

A system including: a processor; and a memory storing instructions thereon that, when executed by the processor, cause the processor to: generate an image including a patient anatomy and one or more implanted medical devices based on performing a long scan process associated with scanning the patient anatomy, wherein generating the image includes sizing a first representation of the patient anatomy and a second representation of the one or more implanted medical devices in the image based on: a pixel size associated with the image; and a focal plane associated with the long scan process; and display the image and a surgical plan associated with the patient anatomy at a user interface of the system, wherein displaying the image and the surgical plan includes at least partially overlaying the surgical plan over the image.

Any of the aspects herein, wherein: the surgical plan includes a graphical model of the one or more implanted medical devices; and displaying the image and the surgical plan includes displaying the graphical model in combination with at least one of: the first representation of the patient anatomy; and the second representation of the one or more implanted medical devices.

Any of the aspects herein, wherein the instructions are further executable by the processor to: scale a size of the graphical model based on the pixel size associated with the image.

Any of the aspects herein, wherein: the surgical plan includes labeling information associated with the patient anatomy; and the instructions are further executable by the processor to position the graphical model with respect to the first representation of the patient anatomy based on: the labeling information; and pixels corresponding to the patient anatomy from among a plurality of pixels associated with the image.

Any of the aspects herein, wherein the instructions are further executable by the processor to adjust, based on one or more scaling factors, at least one of: a first size of the first representation of the patient anatomy; a second size of the second representation of the one or more implanted medical devices; and a third size of the graphical model of the one or more implanted medical devices.

Any of the aspects herein, wherein the instructions are further executable by the processor to: scale a size of the first representation of the patient anatomy with reference to a physical size of the patient anatomy in one or more dimensions.

Any of the aspects herein, wherein the instructions are further executable by the processor to: scale a size of the second representation of the one or more implanted medical devices with reference to a physical size of the one or more implanted medical devices in one or more dimensions.

Any of the aspects herein, wherein the instructions are further executable by the processor to: update a pixel size associated with the image based on a change in focus level associated with generating the image, wherein displaying the image is based on the updated pixel size.

In some aspects, the techniques described herein relate to a method including: generating an image including a patient anatomy and one or more implanted medical devices based on performing a long scan process associated with scanning the patient anatomy, wherein generating the image includes sizing a first representation of the patient anatomy and a second representation of the one or more implanted medical devices in the image based on: a pixel size associated with the image; and a focal plane associated with the long scan process; and displaying the image and a surgical plan associated with the patient anatomy at a user interface, wherein displaying the image and the surgical plan includes at least partially overlaying the surgical plan over the image.

Any aspect in combination with any one or more other aspects.

Any one or more of the features disclosed herein.

Any one or more of the features as substantially disclosed herein.

Any one or more of the features as substantially disclosed herein in combination with any one or more other features as substantially disclosed herein.

Any one of the aspects/features/implementations in combination with any one or more other aspects/features/implementations.

Use of any one or more of the aspects or features as disclosed herein.

It is to be appreciated that any feature described herein can be claimed in combination with any other feature(s) as described herein, regardless of whether the features come from the same described implementation.

The phrases “at least one,” “one or more,” “or,” and “and/or” are open-ended expressions that are both conjunctive and disjunctive in operation. For example, each of the expressions “at least one of A, B and C,” “at least one of A, B, or C,” “one or more of A, B, and C,” “one or more of A, B, or C,” “A, B, and/or C,” and “A, B, or C” means A alone, B alone, C alone, A and B together, A and C together, B and C together, or A, B and C together.

The term "a" or "an" entity refers to one or more of that entity. As such, the terms "a" (or "an"), "one or more," and "at least one" can be used interchangeably herein. It is also to be noted that the terms "comprising," "including," and "having" can be used interchangeably.

The term "automatic" and variations thereof, as used herein, refers to any process or operation, which is typically continuous or semi-continuous, done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material."

Aspects of the present disclosure may take the form of an implementation that is entirely hardware, an implementation that is entirely software (including firmware, resident software, micro-code, etc.) or an implementation combining software and hardware aspects that may all generally be referred to herein as a "circuit," "module," or "system." Any combination of one or more computer-readable medium(s) may be utilized. The computer-readable medium may be a computer-readable signal medium or a computer-readable storage medium.

A computer-readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer-readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer-readable storage medium may be any tangible medium that can contain or store a program for use by or in connection with an instruction execution system, apparatus, or device.

A computer-readable signal medium may include a propagated data signal with computer-readable program code embodied therein, for example, in baseband or as part of a carrier wave. Such a propagated signal may take any of a variety of forms, including, but not limited to, electro-magnetic, optical, or any suitable combination thereof. A computer-readable signal medium may be any computer-readable medium that is not a computer-readable storage medium and that can communicate, propagate, or transport a program for use by or in connection with an instruction execution system, apparatus, or device. Program code embodied on a computer-readable medium may be transmitted using any appropriate medium, including, but not limited to, wireless, wireline, optical fiber cable, RF, etc., or any suitable combination of the foregoing.

The terms "determine," "calculate," "compute," and variations thereof, as used herein, are used interchangeably and include any type of methodology, process, mathematical operation or technique.

The following statements provide non-limiting examples of systems and methods for surgical imaging of the present disclosure:

Statement 1. An imaging system comprising: a processor coupled with the imaging system; and a memory storing instructions thereon that, when executed by the processor, cause the processor to: perform a preview scan process associated with scanning a patient anatomy, wherein performing the preview scan process comprises capturing one or more localization images comprising a portion of the patient anatomy; and capture one or more multidimensional images comprising at least the portion of the patient anatomy based on target coordinates associated with the one or more localization images.

Statement 2. The imaging system of Statement 1, wherein the instructions are further executable by the processor to: based on the target coordinates, generate movement data associated with positioning or orienting at least one of a radiation source, a detector, a rotor, and a gantry of the imaging system in association with capturing the one or more multidimensional images.

Statement 3. The imaging system of Statement 2, wherein the instructions are further executable by the processor to: control the positioning or orienting of at least one of the radiation source, the detector, the rotor, and the gantry based on the movement data.

Statement 4. The imaging system of Statement 2, wherein the instructions are further executable by the processor to: display guidance information associated with the positioning or orienting of at least one of the radiation source, the detector, the rotor, and the gantry based on the movement data.

Statement 5. The imaging system of Statement 2, wherein generating the movement data is based on: a pixel size associated with the one or more localization images; and a focal plane associated with the preview scan process.

Statement 6. The imaging system of any preceding Statement, wherein the one or more localization images comprise: a first localization image of a first image type comprising the portion of the patient anatomy; and a second localization image of a second image type comprising the portion of the patient anatomy, wherein capturing the one or more multidimensional images is based on at least one of the first localization image and the second localization image.

Statement 7. The imaging system of any preceding Statement, wherein the instructions are further executable by the processor to: set the target coordinates in response to a user input associated with the imaging system.

Statement 8. The imaging system of Statement 7, wherein the user input comprises an input via at least one of: a display; a controller device; and an audio input device.

Statement 9. The imaging system of any preceding Statement, wherein the instructions are further executable by the processor to: generate a field of view representation of the patient anatomy comprising the one or more localization images; and update the field of view representation based on the target coordinates.

Statement 10. The imaging system of any preceding Statement, wherein the instructions are further executable by the processor to: capture one or more second localization images comprising the portion of the patient anatomy based on the target coordinates, wherein capturing the one or more multidimensional images is based on: the one or more second localization images; one or more second target coordinates associated with the one or more second localization images; or both.

Statement 11. The imaging system of any preceding Statement, wherein the instructions executable to capture the one or more multidimensional images are further executable by the processor to capture an image volume comprising at least the portion of the patient anatomy based on image data of the one or more multidimensional images.

Statement 12. The imaging system of any preceding Statement, wherein the instructions are further executable by the processor to generate a long scan image comprising at least the portion of the patient anatomy based on image data of the one or more multidimensional images.

Statement 13. The imaging system of any preceding Statement, wherein each of the one or more localization images is: an anterior-posterior image, a posterior-anterior image, a lateral image, an oblique image, an axial image, a coronal image, or a sagittal image.

Statement 14. The imaging system of any preceding Statement, wherein capturing the one or more localization images is based on: one or more positions of a radiation source of the imaging system; and pose information of a subject with respect to the imaging system.

Statement 15. The imaging system of any preceding Statement, wherein the instructions are further executable by the processor to: display orientation information associated with the patient anatomy and the one or more localization images.

Statement 16. The imaging system of any preceding Statement, wherein: the one or more localization images comprise a first localization image and a second localization image; and the instructions are further executable by the processor to: pause setting of second target coordinates in association with the second localization image in response to detecting an active user input of setting first target coordinates in association with the first localization image; and enable the setting of the second target coordinates in response to detecting completion of the active user input.

Statement 17. A system comprising: a processor; and a memory storing instructions thereon that, when executed by the processor, cause the processor to: perform a preview scan process associated with scanning a patient anatomy, wherein performing the preview scan process comprises capturing one or more localization images comprising a portion of the patient anatomy; and capture one or more multidimensional images comprising at least the portion of the patient anatomy based on target coordinates associated with the one or more localization images.

Statement 18. The system of Statement 17, wherein the instructions are further executable by the processor to: based on the target coordinates, generate movement data associated with positioning or orienting at least one of a radiation source, a detector, a rotor, and a gantry of the system in association with capturing the one or more multidimensional images.

Statement 19. The system of Statement 18, wherein the instructions are further executable by the processor to: control the positioning or orienting of at least one of the radiation source, the detector, the rotor, and the gantry based on the movement data; display guidance information associated with the positioning or orienting of at least one of the radiation source, the detector, the rotor, and the gantry based on the movement data; or a combination thereof.

Statement 20. A method comprising: performing, by an imaging system, a preview scan process associated with scanning a patient anatomy, wherein performing the preview scan process comprises capturing one or more localization images comprising a portion of the patient anatomy; and capturing one or more multidimensional images comprising at least the portion of the patient anatomy based on target coordinates associated with the one or more localization images.

Statement 21. An imaging system comprising: a processor coupled with the imaging system; and a memory storing instructions thereon that, when executed by the processor, cause the processor to: generate an image comprising a patient anatomy and one or more implanted medical devices based on performing a long scan process associated with scanning the patient anatomy, wherein generating the image comprises sizing a first representation of the patient anatomy and a second representation of the one or more implanted medical devices in the image based on: a pixel size associated with the image; and a focal plane associated with the long scan process; and display the image and a surgical plan associated with the patient anatomy at a user interface of the imaging system, wherein displaying the image and the surgical plan comprises at least partially overlaying the surgical plan over the image.

Statement 22. The imaging system of Statement 21, wherein: the surgical plan comprises a graphical model of the one or more implanted medical devices; and displaying the image and the surgical plan comprises displaying the graphical model in combination with at least one of: the first representation of the patient anatomy; and the second representation of the one or more implanted medical devices.

Statement 23. The imaging system of Statement 22, wherein the instructions are further executable by the processor to: scale a size of the graphical model based on the pixel size associated with the image.

Statement 24. The imaging system of Statement 22, wherein: the surgical plan comprises labeling information associated with the patient anatomy; and the instructions are further executable by the processor to position the graphical model with respect to the first representation of the patient anatomy based on: the labeling information; and pixels corresponding to the patient anatomy from among a plurality of pixels associated with the image.

Statement 25. The imaging system of Statement 22, wherein the instructions are further executable by the processor to adjust, based on one or more scaling factors, at least one of: a first size of the first representation of the patient anatomy; a second size of the second representation of the one or more implanted medical devices; and a third size of the graphical model of the one or more implanted medical devices.

Statement 26. The imaging system of any preceding Statement, wherein the image comprises a long scan image.

Statement 27. The imaging system of any preceding Statement, wherein the instructions are further executable by the processor to: scale a size of the first representation of the patient anatomy with reference to a physical size of the patient anatomy in one or more dimensions.

Statement 28. The imaging system of any preceding Statement, wherein the instructions are further executable by the processor to: scale a size of the second representation of the one or more implanted medical devices with reference to a physical size of the one or more implanted medical devices in one or more dimensions.

Statement 29. The imaging system of any preceding Statement, wherein the instructions are further executable by the processor to: update a pixel size associated with the image based on a change in focus level associated with generating the image, wherein displaying the image is based on the updated pixel size.

Statement 30. The imaging system of any preceding Statement, wherein: the surgical plan comprises one or more preoperative images, one or more reference intraoperative images, or both; and the image comprises one or more second intraoperative images, one or more postoperative images, or both.

Statement 31. The imaging system of any preceding Statement, wherein the image comprises an X-ray image, a computed tomography (CT) image, or a magnetic resonance imaging (MRI) image.

Statement 32. A system comprising: a processor; and a memory storing instructions thereon that, when executed by the processor, cause the processor to: generate an image comprising a patient anatomy and one or more implanted medical devices based on performing a long scan process associated with scanning the patient anatomy, wherein generating the image comprises sizing a first representation of the patient anatomy and a second representation of the one or more implanted medical devices in the image based on: a pixel size associated with the image; and a focal plane associated with the long scan process; and display the image and a surgical plan associated with the patient anatomy at a user interface of the system, wherein displaying the image and the surgical plan comprises at least partially overlaying the surgical plan over the image.

Statement 33. The system of Statement 32, wherein: the surgical plan comprises a graphical model of the one or more implanted medical devices; and displaying the image and the surgical plan comprises displaying the graphical model in combination with at least one of: the first representation of the patient anatomy; and the second representation of the one or more implanted medical devices.

Statement 34. The system of Statement 33, wherein the instructions are further executable by the processor to: scale a size of the graphical model based on the pixel size associated with the image.

Statement 35. The system of Statement 33, wherein: the surgical plan comprises labeling information associated with the patient anatomy; and the instructions are further executable by the processor to position the graphical model with respect to the first representation of the patient anatomy based on: the labeling information; and pixels corresponding to the patient anatomy from among a plurality of pixels associated with the image.

Statement 36. The system of Statement 33, wherein the instructions are further executable by the processor to adjust, based on one or more scaling factors, at least one of: a first size of the first representation of the patient anatomy; a second size of the second representation of the one or more implanted medical devices; and a third size of the graphical model of the one or more implanted medical devices.

Statement 37. The system of any preceding Statement, wherein the instructions are further executable by the processor to: scale a size of the first representation of the patient anatomy with reference to a physical size of the patient anatomy in one or more dimensions.

Statement 38. The system of any preceding Statement, wherein the instructions are further executable by the processor to: scale a size of the second representation of the one or more implanted medical devices with reference to a physical size of the one or more implanted medical devices in one or more dimensions.

Statement 39. The system of any preceding Statement, wherein the instructions are further executable by the processor to: update a pixel size associated with the image based on a change in focus level associated with generating the image, wherein displaying the image is based on the updated pixel size.

Statement 40. A method comprising: generating an image comprising a patient anatomy and one or more implanted medical devices based on performing a long scan process associated with scanning the patient anatomy, wherein generating the image comprises sizing a first representation of the patient anatomy and a second representation of the one or more implanted medical devices in the image based on: a pixel size associated with the image; and a focal plane associated with the long scan process; and displaying the image and a surgical plan associated with the patient anatomy at a user interface, wherein displaying the image and the surgical plan comprises at least partially overlaying the surgical plan over the image.

What is claimed is:

1. An imaging system comprising:

a processor coupled with the imaging system; and a memory storing instructions thereon that, when executed by the processor, cause the processor to:

receive first and second localization images captured in a preview scan of a patient anatomy, wherein the first localization image comprises the patient anatomy captured from a first view, and the second localization image comprises the patient anatomy captured from a second view different than the first view;

set, based on user input to a user interface, target coordinates on a portion of the patient anatomy within at least one of the first localization image and the second localization image; and generate, based on the target coordinates, movement data for causing at least one component of the imaging system to move to a location for capturing one or more multidimensional images of the portion of the patient anatomy in a scan subsequent to the preview scan.

2. The imaging system of claim 1, wherein the at least one component of the imaging system comprises a radiation source, a detector, a rotor, or a gantry.

3. The imaging system of claim 1, wherein the instructions are further executable by the processor to:

control the positioning or orienting of the at least one component of the imaging system based on the movement data.

4. The imaging system of claim 2, wherein the instructions are further executable by the processor to:

display guidance information associated with the positioning or orienting of the at least one component of the imaging system based on the movement data.

5. The imaging system of claim 1, wherein generating the movement data is based on:

a pixel size associated with the first and second localization images; and a focal plane associated with the preview scan.

6. The imaging system of claim 1, wherein the first view corresponds to an AP or PA view of the patient anatomy, and the second view corresponds to a LAT view of the patient anatomy.

7. The imaging system of claim 1, wherein the instructions are further executable by the processor to:

perform the scan subsequent to the preview scan to capture the one or more multidimensional images comprising at least the portion of the patient anatomy.

8. The imaging system of claim 7, wherein the user input comprises an input via at least one of: a display; a controller device; and an audio input device.

9. The imaging system of claim 7, wherein the first and second localization images are captured based on:

one or more positions of a radiation source of the imaging system; and pose information of a subject with respect to the imaging system.

10. The imaging system of claim 1, wherein the instructions are further executable by the processor to:

generate a field of view representation of the patient anatomy comprising the first and second localization images; and update the field of view representation based on the target coordinates.

11. The imaging system of claim 1, wherein the movement data is generated based on the target coordinates and coordinates which correspond to an isocenter of an imaging device of the imaging system.

12. The imaging system of claim 1, wherein the one or more multidimensional images include an image volume comprising at least the portion of the patient anatomy.

13. The imaging system of claim 1, wherein the instructions are further executable by the processor to generate a long scan image comprising at least the portion of the patient anatomy based on image data of the one or more multidimensional images.

14. The imaging system of claim 1, wherein the first localization image comprises: an anterior-posterior image, a posterior-anterior image, a lateral image, an oblique image, an axial image, a coronal image, or a sagittal image.

15. The imaging system of claim 1, wherein the instructions are further executable by the processor to:

display orientation information associated with the patient anatomy and the first and second localization images.

16. The imaging system of claim 1, wherein:

the instructions are further executable by the processor to:

pause setting of the target coordinates within the second localization image in response to detecting the user input of setting the target coordinates within the first localization image; and enable the setting of the target coordinates within the second localization image in response to detecting completion of the user input for setting the target coordinates within the first localization image.

17. A system comprising:

a processor; and a memory storing instructions thereon that, when executed by the processor, cause the processor to:

receive first and second localization images captured in a preview scan of a patient anatomy, wherein the first localization image comprises the patient anatomy captured from a first view, and the second localization image comprises the patient anatomy captured from a second view different than the first view;

set, based on user input to a user interface, target coordinates on a portion of the patient anatomy within at least one of the first localization image and the second localization image; and generate, based on the target coordinates, movement data for causing at least one component of an imaging system to move to a location for capturing one or more multidimensional images of the portion of the patient anatomy in a scan subsequent to the preview scan.

18. The system of claim 17, wherein the at least one component of the imaging system comprises a radiation source, a detector, a rotor, or a gantry.

19. The system of claim 17, wherein the instructions are further executable by the processor to:

control the positioning or orienting of the at least one component of the imaging system based on the movement data;

display guidance information associated with the positioning or orienting of the at least one component of the imaging system based on the movement data; or a combination thereof.

20. A method comprising:

receiving first and second localization images captured in a preview scan of a patient anatomy, wherein the first localization image comprises the patient anatomy captured from a first view, and the second localization image comprises the patient anatomy captured from a second view different than the first view;

setting, based on user input to a user interface, target coordinates on a portion of the patient anatomy within at least one of the first localization image and the second localization image;

generating, based on the target coordinates, movement data for causing at least one component of an imaging system to move to a location for capturing one or more multidimensional images of the portion of the patient anatomy in a scan subsequent to the preview scan; and controlling the at least one component of the imaging system to move to the location for capturing the one or more multidimensional images of the portion of the patient anatomy.

* * * * *